United States Patent [19]

Ooms et al.

[11] Patent Number: 5,061,310
[45] Date of Patent: Oct. 29, 1991

[54] HERBICIDAL N-PHENYL-SUBSTITUTED OXAZINEDIONES AND OXAZINONETHIONES

[75] Inventors: Pieter Ooms, Krefeld; Franz Kunisch, Odenthal; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 421,888

[22] Filed: Oct. 16, 1989

[30] Foreign Application Priority Data

Oct. 28, 1988 [DE] Fed. Rep. of Germany ....... 3836742

[51] Int. Cl.$^5$ ................... A01N 43/00; C07D 265/12
[52] U.S. Cl. ......................... 71/88; 544/92; 544/97
[58] Field of Search ............... 544/92, 97; 71/65, 88, 71/90

[56] References Cited

U.S. PATENT DOCUMENTS 3,697,517 10/1972 Kurz et al. ............................ 544/92
3,931,171 6/1976 Jager et al. ............................ 544/97

FOREIGN PATENT DOCUMENTS 2132763 1/1973 Fed. Rep. of Germany .
50049424 3/1973 Japan ..................................... 71/88

OTHER PUBLICATIONS

Wagner G. "Preparation of 2-Hydroxythiobenzanilides . . . ", CA 59:8728g (1963).
G. Wagner and D. Singer "Zur Darstellung von 2-Hydroxythiobenzaniliden und 3-Aryl-mono und Di-thiobenzoxazinen-(1,3)", Z. Chem. 3 Heft 4 (1963).
Chemical Abstracts, vol. 89, No. 17, Oct. 23, 1978 "Syntheses . . . H-Nucleophiles", (89:146867x).
Chemical Abstracts, vol. 87, No. 21, Nov. 21, 1977, "Oxazine Derivatives", (87:168049t).
Chemical Abstracts, vol. 74, No. 11, Mar. 15, 1971, "3,4-Dihydro . . . Pyrones", (53811z).

*Primary Examiner*—C. Warren Ivy
*Assistant Examiner*—Celia Chang
*Attorney, Agent, or Firm*—Sprung Horn Kramer & Woods

[57] ABSTRACT

Combating unwanted vegetation with N-phenyl-substituted oxazinediones of the formula

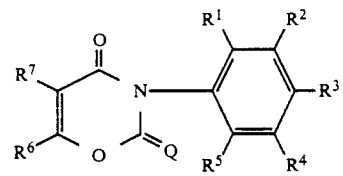

in which
$R^1$, $R^2$, $R^3$, $R^4$, $R^5$, $R^6$ and $R^7$ can each be hydrogen or an organic radical or $R^2$ and $R^3$ and/or $R^6$ and $R^7$ can form a ring, and
Q is oxygen or sulphur.

Those compounds are new wherein at least three of the radicals $R^1$ to $R^5$ are other than hydrogen or the two radicals $R^2$ and $R^3$ together represent —O—CH$_2$—O—CH$_2$— or the group —X—(CO)$_n$—A—Y—.

5 Claims, No Drawings

HERBICIDAL N-PHENYL-SUBSTITUTED OXAZINEDIONES AND OXAZINONETHIONES

The invention relates to the use of novel and known N-phenyl-substituted oxazinediones as herbicides, and to novel N-phenyl-substituted oxazinediones and several processes for the preparation thereof.

It has been disclosed that certain heterocyclic compounds, such as, for example, 4-amino-3-methyl-6-phenyl-4H-1,2,4-triazin-5-one (Metamitron, GOLTIX) are herbicidally active (cf. DE-OS (German Published Specification) 2,364,474). However, the action of this known compound is not satisfactory in all respects.

Furthermore, a series of substituted oxazinediones are known from the literature, but not their herbicidal properties (cf. Chem. Ber. 109 (1976), 2456-2461; Tetrahedron Lett. 1967, 2089-2092; Liebigs Ann. Chem. 1976, 1689-1712; J. Heterocycl. Chem. 18 (1981), 1095-1100; J. Org. Chem. 49 (1984), 5105-5108; Monatsh. Chem. 94 (1963), 544-548; DE-OS (German Published Specification) 2,132,763; DE-AS (German Published Specification) 2,207,549; DE-OS (German Published Specification) 2,005,118).

In the present application, the novel N-phenyl-substituted oxazinediones described first are those of the formula (I) and the novel and known N-phenyl-substituted oxazinediones which are described later are those of the formula (IA).

Novel substituted oxazinediones of the general formula (I)

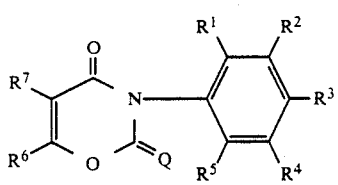

in which $R^1$ represents hydrogen or halogen, $R^2$ represents hydrogen, halogen, nitro, cyano or an optionally substituted radical from the series comprising alkyl, alkenyl, alkinyl, alkoxy, alkenyloxy, alkinyloxy, alkylthio, alkenylthio, alkinylthio, alkylsulphinyl, alkylsulphonyl and alkylamino, $R^3$ represents hydrogen, halogen, nitro, cyano or an optionally substituted radical from the series comprising alkyl, alkenyl, alkinyl, alkoxy, alkenyloxy, alkinyloxy, alkylthio, alkenylthio, alkinylthio, alkylsulphinyl, alkylsulphonyl and alkylamino, or the two radicals $R^2$ and $R^3$ together represent —O—CH$_2$—O—CH$_2$—or the group —X—(CO)$_n$—A—Y—where n represents the numbers 0 or 1, A represents a direct bond or represents straight-chain or branched and optionally halogen-substituted alkanediyl, X represents oxygen, sulphur or the group N—R$^8$ where $R^8$ represents hydrogen or optionally substituted alkyl, alkenyl or alkinyl, and Y represents oxygen or sulphur, $R^4$ represents hydrogen or halogen, $R^5$ represents hydrogen or halogen, $R^6$ represents hydrogen, halogen or optionally substituted alkyl, $R^7$ represents hydrogen, halogen or optionally substituted alkyl, or the two radicals $R^6$ and $R^7$ together represent straight-chain or branched alkanediyl or together with the carbon atoms to which they are bonded form a benzo group, and Q represents oxygen or sulphur, the proviso that at least three of the radicals $R^1$ to $R^5$ are other than hydrogen or the two radicals $R^2$ and $R^3$ together represent —O—CH$_2$—O—CH$_2$—or the group —X—(CO)$_n$—A—Y—, have now been found.

The novel N-phenyl-substituted oxazinediones of the general formula (I) are obtained when aryl iso(thio)cyanates of the general formula (II)

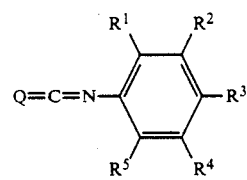

in which

Q, $R^1$, $R^2$, $R^3$, $R^4$ and $R^5$ have the abovementioned meanings, (a) are reacted with 1,3-dioxin-4-ones of the general formula (III)

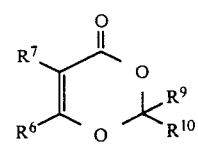

in which $R^6$ and $R^7$ have the abovementioned meanings and $R^9$ and $R^{10}$ represent hydrogen or optionally substituted alkyl, if appropriate in the presence of a diluent, or (b) are reacted with dicarboxylic acid dichlorides of the general formula (IV)

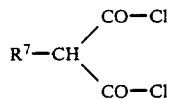

in which $R^7$ has the abovementioned meaning, if appropriate in the presence of a diluent, or (c) are reacted with 2-diazo-1,3-diketones of the general formula (V)

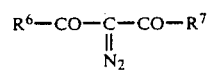

in which $R^6$ and $R^7$ have the abovementioned meanings, if appropriate in the presence of a diluent, or (d) are reacted with a salicylic acid or its esters of the general formula (VI)

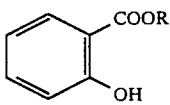

in which

R represents hydrogen or alkyl, if appropriate in the presence of an acid acceptor and if appropriate in the presence of a diluent.

Other synthesis routes for the substituted oxazinediones are outlined below, $R^1$ to $R^{10}$ and Q having the abovementioned meanings:

(e) reaction of aryl iso)(thio)cyanates (II) with 5-acyl-1,3-diozane-4,5-diones (VII):

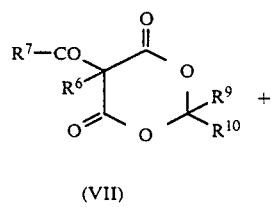

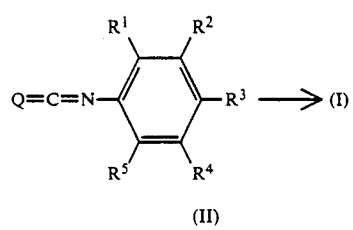

(f) reaction of aryl iso(thio)cyanates (II) with diketenes (VIII):

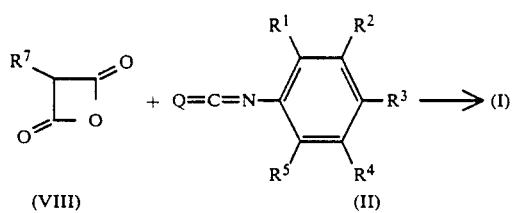

(g) reaction of aryl iso(thio)cyanates (II) with ethoxyalkinones (IX) - (R: $C_2H_5$):

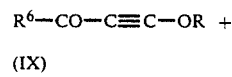

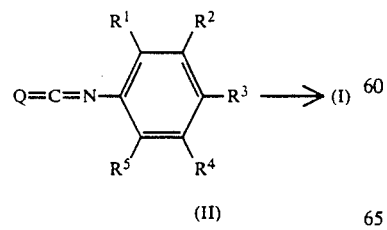

(h) reaction of oxazinediones (Ia) with halogens ($X_2$: chlorine or bromine):

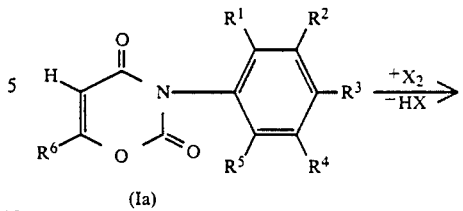

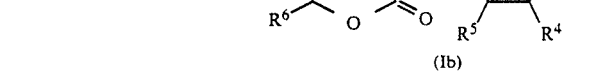

The novel substituted oxazinediones of the general formula (I) are distinguished by a powerful herbicidal activity. The compounds of the formula (I) which are excluded above by a disclaimer also show a very good herbicidal activity.

In the definitions, the saturated or unsaturated hydrocarbon chains, such as, for example, alkyl, alkoxy, alkylsulphonyl, alkenyl, alkinyl, alkenyloxy or cycloalkylalkyl, are in each case straight-chain or branched.

In the list, the combination of the radicals with "and-/or" means that the compounds can be monosubstituted or polysubstituted by identical or different substituents.

Halogen in general represents fluorine, chlorine, bromine or iodine. Halogen preferably represents fluorine, chlorine or bromine.

The invention relates then to the use of the novel compounds of the formula (I) according to the invention and of the known substituted oxazinediones, which are embraced by the formula (IA) below,

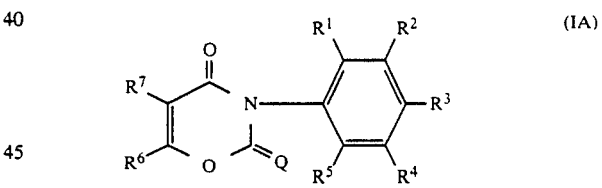

in which $R^1$ represents hydrogen or halogen, $R^2$ represents hydrogen, halogen, nitro, cyano or an optionally substituted radical from the series comprising alkyl, alkenyl, alkinyl, alkoxy, alkenyloxy, alkinyloxy, alkylthio, alkenylthio, alkinylthio, alkylsulphinyl, alkylsulphonyl and alkylamino, $R^3$ represents hydrogen, halogen, nitro, cyano or an optionally substituted radical from the series comprising alkyl, alkenyl, alkinyl, alkoxy, alkenyloxy, alkinyloxy, alkylthio, alkenylthio, alkinylthio, alkylsulphinyl, alkylsulphonyl and alkylamino, or the two radicals $R^2$ and $R^3$ together represent —O—$CH_2$—O—$CH_2$— or the group —X—$(CO)_n$—A—Y—where n represents the numbers 0 or 1, A represents a direct bond or represents straight-chain or branched and optionally halogen-substituted alkanediyl, X represents oxygen, sulphur or the group N—$R^8$ where $R^8$ represents hydrogen or optionally substituted alkyl, alkenyl or alkinyl, and Y represents oxygen or sulphur, in which furthermore $R^4$ represents hydrogen or halogen, $R^5$ represents hydrogen or halogen, $R^6$ represents hydrogen, halogen or optionally substituted alkyl, $R^7$ represents hydrogen, halogen or optionally substituted alkyl, or the two radicals $R^6$ and $R^7$ together represent straight-chain or branched alkanediyl or together with the carbon atoms to which they are bonded form a benzo group, and Q represents oxygen or sulphur.

Surprisingly, the substituted oxazinediones of the general formula (I) or (IA) according to the invention have a considerably more powerful activity against important weeds than, for example, 4-amino-3-methyl-6-phenyl-4H-1,2,4,-triazin-5-one, which is a previously known active compound of similar structure and identical direction of action.

The invention preferably relates to compounds of the general formula (I) in which $R^1$ represents hydrogen or halogen, $R^2$ represents hydrogen, nitro, cyano, halogen, or represents a radical from the series comprising $C_1$–$C_8$-alkyl, $C_1$–$C_6$-alkoxy, $C_1$–$C_6$-alkylthio and $C_1$–$C_6$-alkylamino, which radical is optionally substituted by fluorine, chlorine, bromine, cyano, $C_3$–$C_6$-cycloalkyl which is optionally substituted by fluorine, chlorine, bromine, methyl an d/or ethyl, by $C_1$–$C_6$-alkoxy, $C_1$–$C_4$-alkoxy-$C_1$–$C_4$-alkoxy, $C_1$–$C_6$-alkylthio, $C_1$–$C_6$-alkylsulphinyl, $C_1$–$C_6$-alkylsulphonyl, $C_1$–$C_4$-alkylthio-$C_1$–$C_4$-alkoxy, $C_1$–$C_4$-alkylsulphonyl-$C_1$–$C_4$-alkoxy, $C_3$–$C_6$-alkenyloxy, $C_3$–$C_6$-alkinyloxy, $C_3$–$C_6$-alkenylthio, $C_3$–$C_6$-alkinylthio, carboxyl, $C_1$–$C_6$-alkoxy-carbonyl, $C_3$–$C_6$-alkenyloxy-carbonyl, $C_3$–$C_6$-alkinyloxy-carbonyl, $C_3$–$C_6$-cycloalkyloxy-carbonyl, $C_3$–$C_6$-cycloalkenyloxy-carbonyl, $C_3$–$C_6$-cycloalkyl-$C_1$–$C_4$-alkoxy-carbonyl, $C_3$–$C_6$-cycloalkenyl-$C_1$–$C_4$-alkoxy-carbonyl, $C_1$–$C_4$-alkoxy-$C_1$–$C_4$-alkoxy-carbonyl, $C_1$–$C_4$-alkylthio-$C_1$–$C_4$-alkoxy-carbonyl, benzyloxy-$C_1$–$C_4$-alkoxy-carbonyl, $C_1$–$C_4$-alkoxy-carbonyl-$C_1$–$C_4$-alkoxy-carbonyl, $C_1$–$C_4$-alkylamino-carbonyl-$C_1$–$C_4$-alkoxy-carbonyl, di-($C_1$–$C_4$-alkyl)-amino-carbonyl-$C_1$–$C_4$-alkoxy-carbonyl, $C_1$–$C_4$-alkoxy-$C_1$–$C_4$-alkoxy-$C_1$–$C_4$-alkyl-amino-carbonyl, $C_1$–$C_4$-alkoxy-imino-$C_1$–$C_4$-alkyl, $C_3$–$C_4$-alkenyloxy-imino-$C_1$–$C_4$-alkyl, $C_1$–$C_6$-alkylthio-carbonyl-$C_1$–$C_4$-alkoxy-imino-$C_1$–$C_4$-alkyl, $C_1$–$C_6$-alkylthio-carbonyl, $C_3$–$C_6$-alkenylthio-carbonyl, $C_3$–$C_6$-alkinylthio-carbonyl, carbamoyl, $C_1$–$C_6$-alkylamino-carbonyl, $C_3$–$C_6$-alkenylamino-carbonyl, $C_3$–$C_6$-alkinylamino-carbonyl, di-($C_1$–$C_4$-alkyl)-amino-carbonyl, di-($C_3$–$C_4$-alkenyl)amino-carbonyl and/or di-($C_3$–$C_4$-alkinyl)-aminocarbonyl, or represents a radical from the series comprising $C_3$–$C_6$-alkenyl, $C_3$–$C_6$-alkinyl, $C_3$–$C_6$-alkenyloxy, $C_3$–$C_6$-alkinyloxy, $C_3$–$C_6$-alkenylthio, $C_3$–$C_6$-alkinylthio, $C_1$–$C_6$-alkylsulphinyl and $C_1$–$C_6$-alkylsulphonyl, which radical is optionally substituted by fluorine and/or chlorine, $R^3$ represents hydrogen, halogen, nitro, cyano, or represents a radical from the series comprising $C_1$–$C_4$-alkyl, $C_3$–$C_4$-alkenyl, $C_3$–$C_4$-alkinyl, $C_1$–$C_4$-alkoxy, $C_3$–$C_4$-alkenyloxy, $C_3$–$C_4$-alkinyloxy, $C_1$–$C_4$-alkylthio, $C_3$–$C_4$-alkenylthio, $C_3$–$C_4$-alkinylthio, $C_1$–$C_4$-alkylsulphinyl, $C_1$–$C_4$-alkylsulphonyl and $C_1$–$C_4$-alkylamino, which radical is optionally substituted by fluorine and/or chlorine, or the two radicals $R^2$ and $R^3$ together represent —O—$CH_2$O—$CH_2$— or the group —X—(CO)$_n$—A—Y— where n represents the numbers 0 or 1, A represents a direct bond or represents straight-chain or branched $C_1$–$C_4$-alkanediyl which is optionally substituted by fluorine and/or chlorine, X represents oxygen, sulphur or the group N—$R^8$ where $R^8$ represents hydrogen or radicals from the series comprising $C_1$–$C_4$-alkyl, $C_3$–$C_4$-alkenyl and $C_3$–$C_4$-alkinyl, which radicals are optionally substituted by fluorine and/or chlorine, cyano, $C_1$–$C_4$-alkoxy, $C_1$–$C_4$-alkoxy-carbonyl or pyridiyl, and Y represents oxygen or sulphur, in which furthermore $R^4$ represents hydrogen or halogen, $R^5$ represents hydrogen or halogen, $R^6$ represents hydrogen, halogen or $C_1$–$C_4$-alkyl which is optionally substituted by fluorine and/or chlorine, $R^7$ represents hydrogen, halogen or $C_1$–$C_4$-alkyl which is optionally substituted by fluorine and/or chlorine, or the two radicals $R^6$ and $R^7$ together represent straight-chain or branched $C_3C_5$-alkanediyl or together with the carbon atoms to which they are bonded form a benzo group, and Q represents oxygen or sulphur, —with the proviso that at least three of the radicals $R^1$ to $R^5$ are other than hydrogen or the two radicals $R^2$ and $R^3$ together represent —O—$CH_2$—O—$CH_2$—or the group —X—(CO)$_n$—A—Y—.

In particular, the invention relates to compounds of the general formula (I) in which $R^1$ represents hydrogen, $R^2$ represents hydrogen, nitro, cyano, fluorine, chlorine or bromine, or represents a radical from the series comprising $C_1$–$C_4$-alkyl, $C_1$–$C_4$-alkoxy, $C_1$–$C_4$-alkylthio and $C_1$–$C_4$-alkylamino, which radical is optionally substituted by fluorine, chlorine, cyclopropyl which can be substituted by chlorine and/or methyl; by $C_1$–$C_4$-alkoxy, $C_1$–$C_4$-alkylthio, $C_1$–$C_4$-alkylsulphinyl, $C_1$–$C_4$-alkylsulphonyl, $C_3$–$C_4$-alkenyloxy, $C_3$–$C_4$-alkinyloxy, $C_3$–$C_4$-alkenylthio, $C_3$–$C_4$-alkinylthio, carboxyl, $C_1$–$C_4$-alkoxy-carbonyl, $C_3$–$C_4$-alkenyloxy-carbonyl, $C_3$–$C_4$-alkinyloxy-carbonyl, $C_3$–$C_6$-cycloalkyloxy-carbonyl, $C_3$–$C_6$-cycloalkyl-$C_1$–$C_2$-alkoxycarbonyl, $C_1$–$C_1$-alkoxy-$C_1$–$C_2$-alkoxy-carbonyl, $C_1$–$C_4$-alkylthio-$C_1$–$C_2$-alkoxy-carbonyl, $C_1$–$C_4$-alkoxy-carbonyl-$C_1$–$C_2$-alkoxy-carbonyl or $C_1$–$C_4$-alkylaminocarbonyl, di-($C_1$–$C_2$-alkyl)-aminocarbonyl, $C_1$–$C_2$-alkoxy-$C_1$–$C_2$-alkyl-amino-carbonyl, $C_3$–$C_4$-alkenyloxyimino-$C_1$–$C_2$-alkyl, $C_1$–$C_2$-alkoxy-imino-$C_1$–$C_2$-alkyl, $C_1$–$C_2$-alkoxy-carbonyl-$C_1$–$C_2$-alkoxy-imino-$C_1$–$C_2$-alkyl, or represents a radical from the series comprising $C_3$–$C_4$-alkenyloxy, $C_3$–$C_4$-alkinyloxy, $C_3$–$C_4$-alkenylthio and $C_3-C_4$-alkinylthio, which radical is optionally substituted by fluorine and/or chlorine, $R^3$ represents hydrogen, fluorine, chlorine, bromine, cyano, methyl or trifluoromethyl, or the two radicals $R^2$ and $R^3$ together represent —O—CH$_2$—O—CH$_2$—or the group —X—(CO)$_n$—A—Y—where
  n represents the numbers 0 or 1,
  A represents a direct bond or represents methylene, ethylene, propylene or butylene,
  X represents oxygen or the group N—$R^8$ where
    $R^8$ represents hydrogen, $C_1-C_4$-alkyl, $C_3-C_4$-alkenyl or $C_3-C_4$-alkinyl, and
  Y represents oxygen, in which furthermore $R^4$ represents hydrogen, $R^5$ represents hydrogen, fluorine or chlorine $R^6$ represents hydrogen, chlorine, bromine, methyl, ethyl, propyl, isopropyl or trifluoromethyl, $R^7$ represents hydrogen, chlorine, bromine, methyl, ethyl, propyl, isopropyl or trifluoromethyl, or the two radicals $R^6$ and $R^7$ together represent straight-chain or branched $C_3-C_5$-alkanediyl or together with the carbon atoms to which they are bonded form a benzo group, and Q represents oxygen or sulphur, —with the proviso that the radicals $R^2$, $R^3$ and $R^5$ are other than hydrogen or the two radicals $R^2$ and $R^3$ together represent —O—CH$_2$—O—CH$_2$—or the group —X—(CO)$_n$—A—Y—where n, A, X and Y have the meanings mentioned above as particularly preferred.

In the formula (IA), $R^1$, $R^2$, $R^3$, $R^4$, $R^5$, $R^6$, $R^7$ and Q preferably, or in particular, have those meanings which have been indicated in the description of the compounds of the formula (I) as being preferred, or particularly preferred, for $R^1$, $R^2$, $R^3$, $R^4$, $R^5$, $R^6$, $R^7$ and Q.

Examples of the compounds of the formula (I) as well as of the formula (IA) according to the invention are listed in Table 1 which follows.

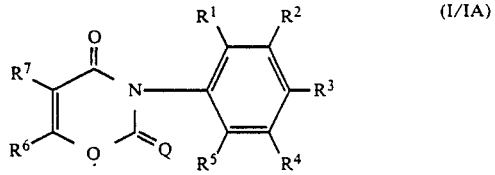

(I/IA)

TABLE 1

| | | Examples of the compounds of the formula (I) or (IA) according to the invention | | | | | |
|---|---|---|---|---|---|---|---|
| $R^1$ | $R^2$ | $R^3$ | $R^4$ | $R^5$ | $R^6$ | $R^7$ | Q |
| H | OCH$_3$ | Cl | H | F | CH$_3$ | H | O |
| H | OCH$_3$ | Cl | H | Cl | CH$_3$ | H | O |
| H | C$_2$H$_5$ | Cl | H | Cl | CH$_3$ | H | O |
| H | OC$_2$H$_5$ | Cl | H | F | CH$_3$ | H | O |
| H | OCH(CH$_3$)$_2$ | Cl | H | F | CH$_3$ | H | O |
| H | OCH(CH$_3$)$_2$ | Cl | H | Cl | CH$_3$ | H | O |
| H | OC$_4$H$_9$ | Cl | H | Cl | CH$_3$ | H | O |
| H | OC$_4$H$_9$ | Cl | H | F | CH$_3$ | H | O |
| H | OCHF$_2$ | Cl | H | F | CH$_3$ | H | O |
| H | OCHF$_2$ | Cl | H | Cl | CH$_3$ | H | O |
| H | OCH$_3$ | Cl | H | Cl | CH$_3$ | H | S |
| H | OCH$_3$ | Cl | H | F | CH$_3$ | H | S |
| H | CH$_3$ | Cl | H | F | CH$_3$ | H | O |
| H | C$_2$H$_5$ | Cl | H | F | CH$_3$ | H | O |
| H | CH$_3$ | Cl | H | Cl | CH$_3$ | H | O |
| H | C$_2$H$_5$ | Cl | H | F | CH$_3$ | H | O |
| H | SCH$_3$ | Cl | H | F | CH$_3$ | H | O |
| H | SCH$_3$ | Cl | H | Cl | CH$_3$ | H | O |
| H | SC$_2$H$_5$ | Cl | H | Cl | CH$_3$ | H | O |
| H | SC$_2$H$_5$ | Cl | H | F | CH$_3$ | H | O |
| H | OCH$_2$COOCH$_3$ | Cl | H | Cl | CH$_3$ | H | O |
| H | OCH$_2$COOCH$_3$ | Cl | H | F | CH$_3$ | H | O |
| H | OCH$_2$COOC$_2$H$_5$ | Cl | H | F | CH$_3$ | H | O |
| H | OCH$_2$COOC$_2$H$_5$ | Cl | H | Cl | CH$_3$ | H | O |
| H | OCHCOOCH$_3$<br>\|<br>CH$_3$ | Cl | H | Cl | CH$_3$ | H | O |
| H | OCHCOOCH$_3$<br>\|<br>CH$_3$ | Cl | H | F | CH$_3$ | H | O |
| H | OCHCOOC$_2$H$_5$<br>\|<br>CH$_3$ | Cl | H | F | CH$_3$ | H | O |
| H | OCHCOOC$_2$H$_5$<br>\|<br>CH$_3$ | Cl | H | Cl | CH$_3$ | H | O |
| H | OCH$_2$CH=CH$_2$ | Cl | H | Cl | CH$_3$ | H | O |
| H | OCH$_2$CH=CH$_2$ | Cl | H | F | CH$_3$ | H | O |
| H | OCH$_2$C≡CH | Cl | H | F | CH$_3$ | H | O |
| H | OCH$_2$C≡CH | Cl | H | Cl | CH$_3$ | H | O |
| H | —NH—CO—CH$_2$—O— | | H | H | CH$_3$ | H | O |

TABLE 1-continued

Examples of the compounds of the formula (I) or (IA) according to the invention

| R¹ | R² | R³ | R⁴ | R⁵ | R⁶ | R⁷ | Q |
|---|---|---|---|---|---|---|---|
| H | —NH—CO—CH₂—O— | | H | F | CH₃ | H | O |
| H | —NH—CO—CH₂—O— | | H | Cl | CH₃ | H | O |
| H | Cl | F | Cl | F | CH₃ | H | O |
| H | OCH(CH₃)₂ | Br | H | F | CH₃ | H | O |
| H | OCH₃ | Br | H | F | CH₃ | H | O |
| H | OC₃H₇ | Cl | H | F | CH₃ | H | O |
| H | OCH₂CH(CH₃)₂ | Cl | H | F | CH₃ | H | O |
| H | CH₂COOCH₃ | Cl | H | F | CH₃ | H | S |
| H | OCH₂CH=CH₂ | Cl | H | F | CH₃ | H | S |
| H | OCH₂C≡CH | Cl | H | F | CH₃ | H | S |
| H | OCH₂COOCH₃ | Cl | H | Cl | CH₃ | H | S |
| H | OCH₂CH=CH₂ | Cl | H | Cl | CH₃ | H | S |
| H | OCH₂C≡CH | Cl | H | Cl | CH₃ | H | S |
| H | OCHCH₂CH₃<br>\|<br>CH₃ | Cl | H | F | CH₃ | H | O |
| H | OCH₂COOCH(CH₃)₂ | Cl | H | F | CH₃ | H | O |
| H | OCH₂COO—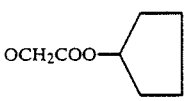 | Cl | H | F | CH₃ | H | O |
| H | OCH₂COOC₅H₁₁ | Cl | H | F | CH₃ | H | O |
| H | OCH₂COOCH₂—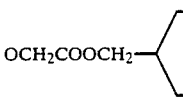 | Cl | H | F | CH₃ | H | O |
| H | OCH₂CH₂OCH₃ | Cl | H | F | CH₃ | H | O |
| H | OCH₂CH₂OC₂H₅ | Cl | H | F | CH₃ | H | O |
| H | OCH₂CH₂SCH₃ | Cl | H | F | CH₃ | H | O |
| H | OCH₂CH₂SC₂H₅ | Cl | H | F | CH₃ | H | O |
| H | SCH₂COOCH₃ | Cl | H | F | CH₃ | H | O |
| H | SCH₂COOC₂H₅ | Cl | H | F | CH₃ | H | O |
| H | SCH₂COOC₅H₁₁ | Cl | H | F | CH₃ | H | O |
| H | SCH₂COO—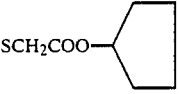 | Cl | H | F | CH₃ | H | O |
| H | SCH₂COOCH₂—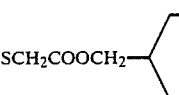 | Cl | H | F | CH₃ | H | O |
| H | SCH(CH₃)₂ | Cl | H | F | CH₃ | H | O |
| H | SC₄H₉ | Cl | H | F | CH₃ | H | O |
| H | SCH₂CH=CH₂ | Cl | H | F | CH₃ | H | O |
| H | SCH₂C≡CH | Cl | H | F | CH₃ | H | O |
| H | OCH₂COOCH₂CH=CH₂ | Cl | H | F | CH₃ | H | O |
| H | OCH₂COOCH₂C≡CH | Cl | H | F | CH₃ | H | O |
| H | OCH₂CON(CH₃)₂ | Cl | H | F | CH₃ | H | O |
| H | OCH₂CON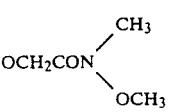 | Cl | H | F | CH₃ | H | O |
| H | OC=N—OCH₃<br>\|<br>CH₃ | Cl | H | F | CH₃ | H | O |
| H | OCH₂CH=N—OCH₃ | Cl | H | F | CH₃ | H | O |
| H | OCHCH=N—OCH₃<br>\|<br>CH₃ | Cl | H | F | CH₃ | H | O |

TABLE 1-continued

Examples of the compounds of the formula (I) or (IA) according to the invention

| R¹ | R² | R³ | R⁴ | R⁵ | R⁶ | R⁷ | Q |
|---|---|---|---|---|---|---|---|
| H | OCH$_2$CH=N—OCH$_2$CH$_2$=CH$_2$ | Cl | H | F | CH$_3$ | H | O |
| H | OCH$_2$CH=N—OCH$_2$COOCH$_3$ | Cl | H | F | CH$_3$ | H | O |
| H | SCH$_2$COOCH$_2$CH=CH$_2$ | Cl | H | F | CH$_3$ | H | O |
| H | SCH$_2$COOCH$_2$C≡CH | Cl | H | F | CH$_3$ | H | O |
| H | OCH$_2$COOCH$_2$COOCH$_3$ | Cl | H | F | CH$_3$ | H | O |
| H | OCH$_2$—CH—CH$_2$ with C(Cl)(Cl) | Cl | H | F | CH$_3$ | H | O |
| H | OCH$_2$—CH—CH—CH$_3$ with C(Cl)(Cl) | Cl | H | F | CH$_3$ | H | O |
| H | OCHF$_2$ | Cl | H | F | CH$_3$ | H | S |
| H | OCF$_2$CHFCl | Cl | H | Cl | CH$_3$ | H | O |
| H | OCF$_2$CHFCl | Cl | H | F | CH$_3$ | H | O |
| H | OCF$_2$CHF$_2$ | Cl | H | F | CH$_3$ | H | O |
| H | OCH$_2$CH=CHCl | Cl | H | F | CH$_3$ | H | O |
| H | OCF$_2$Cl | Cl | H | F | CH$_3$ | H | O |
| H | OCF$_3$ | Cl | H | F | CH$_3$ | H | O |
| H | —N(CH$_2$CH=CH$_2$)—CO—CH$_2$—O— | | H | H | CH$_3$ | H | O |
| H | —N(CH$_2$CH=CH$_2$)—CO—CH$_2$—O— | | H | F | CH$_3$ | H | O |
| H | —N(CH$_2$C≡CH)—CO—CH$_2$—O— | | H | H | CH$_3$ | H | O |
| H | —N(CH$_2$C≡CH)—CO—CH$_2$—O— | | H | F | CH$_3$ | H | O |
| H | OCH$_2$COOC$_5$H$_{11}$ | CH$_3$ | H | F | CH$_3$ | H | O |
| H | OCH$_2$=CH$_2$ | CH$_3$ | H | F | CH$_3$ | H | O |
| H | OCH$_2$C≡CH | CH$_3$ | H | F | CH$_3$ | H | O |
| H | OCH$_2$COOCH$_2$C≡CH | CH$_3$ | H | F | CH$_3$ | H | O |
| H | OCH$_2$COO-cyclopentyl | CH$_3$ | H | F | CH$_3$ | H | O |
| H | SCH$_2$COO-cyclopentyl | CH$_3$ | H | F | CH$_3$ | H | O |
| H | SCH$_2$COOCH$_2$C≡CH | CH$_3$ | H | F | CH$_3$ | H | O |
| H | (OCH$_2$CH$_2$)$_2$OC$_2$H$_5$ | Br | H | F | CH$_3$ | H | S |
| H | (OCH$_2$CH$_2$)$_2$OC$_2$H$_5$ | Cl | H | F | CH$_3$ | H | O |
| H | (OCH$_2$CH$_2$)$_2$OCH$_3$ | Cl | H | F | CH$_3$ | H | O |
| H | OCH$_3$ | Cl | H | Cl | | —(CH$_2$)$_3$— | O |
| H | OCH$_3$ | Cl | H | F | | —(CH$_2$)$_3$— | O |
| H | OCH$_3$ | Cl | H | F | | —(CH$_2$)$_4$— | O |
| H | OCH$_3$ | Cl | H | Cl | | —(CH$_2$)$_4$— | O |
| H | OC$_2$H$_5$ | Cl | H | F | | —(CH$_2$)$_3$— | O |
| H | OC$_2$H$_5$ | Cl | H | F | | —(CH$_2$)$_4$— | O |
| H | OC$_3$H$_7$ | Cl | H | F | | —(CH$_2$)$_3$— | O |
| H | OCH(CH$_3$)$_2$ | Cl | H | F | | —(CH$_2$)$_3$— | O |
| H | OC$_4$H$_9$ | Cl | H | F | | —(CH$_2$)$_3$— | O |
| H | OCH$_2$CH(CH$_3$)$_2$ | Cl | H | F | | —(CH$_2$)$_3$— | O |
| H | OCH$_2$CH=CH$_2$ | Cl | H | F | | —(CH$_2$)$_3$— | O |
| H | OCH$_2$C≡CH | Cl | H | F | | —(CH$_2$)$_3$— | O |
| H | OCH$_2$COOCH$_3$ | Cl | H | F | | —(CH$_2$)$_3$— | O |
| H | OCH$_3$ | Cl | H | F | | —(CH$_2$)$_3$— | S |
| H | OCH(CH$_3$)$_2$ | Cl | H | F | | —(CH$_2$)$_3$— | S |

TABLE 1-continued

Examples of the compounds of the formula (I) or (IA) according to the invention

| R¹ | R² | R³ | R⁴ | R⁵ R⁶ | R⁷ | Q |
|---|---|---|---|---|---|---|
| H | OCH$_2$COOCH$_3$ | Cl | H | F | —(CH$_2$)$_3$— | S |
| H | OCHF$_2$ | Cl | H | F | —(CH$_2$)$_3$— | S |
| H | OCHF$_2$ | Cl | H | F | —(CH$_2$)$_3$— | O |
| H | OCHF$_2$ | Cl | H | F | —(CH$_2$)$_4$— | O |
| H | CH$_3$ | Cl | H | F | —(CH$_2$)$_3$— | O |
| H | C$_2$H$_5$ | Cl | H | F | —(CH$_2$)$_3$— | O |
| H | SCH$_3$ | Cl | H | Cl | —(CH$_2$)$_3$— | O |
| H | SCH$_3$ | Cl | H | F | —(CH$_2$)$_3$— | O |
| H | SC$_2$H$_5$ | Cl | H | F | —(CH$_2$)$_3$— | O |
| H | SC$_2$H$_5$ | Cl | H | F | —(CH$_2$)$_4$— | O |
| H | OCH$_2$COOCH$_3$ | Cl | H | F | —(CH$_2$)$_4$— | O |
| H | OCH$_2$COOC$_2$H$_5$ | Cl | H | F | —(CH$_2$)$_3$— | O |
| H | OCHCOOCH$_3$<br>\|<br>CH$_3$ | Cl | H | F | —(CH$_2$)$_3$— | O |
| H | OCHCOOC$_2$H$_5$<br>\|<br>CH$_3$ | Cl | H | F | —(CH$_2$)$_3$— | O |
| H | —NH—CO—CH$_2$—O— | | H | H | —(CH$_2$)$_3$— | O |
| H | —NH—CO—CH$_2$—O— | | H | F | —(CH$_2$)$_3$— | O |
| H | —NH—CO—CH$_2$—O— | | H | Cl | —(CH$_2$)$_3$— | O |
| H | OCH$_3$ | Br | H | F | —(CH$_2$)$_3$— | O |
| H | OCH$_2$COO—⟨cyclopentyl⟩ | Cl | H | F | —(CH$_2$)$_3$— | O |
| H | OCH$_2$COOC$_5$H$_{11}$ | Cl | H | F | —(CH$_2$)$_3$— | O |
| H | OCH$_2$COOCH$_2$—⟨cyclopentyl⟩ | Cl | H | F | —(CH$_2$)$_3$— | O |
| H | OCH$_2$CH$_2$OCH$_3$ | Cl | H | F | —(CH$_2$)$_3$— | O |
| H | OCH$_2$CH$_2$OC$_2$H$_5$ | Cl | H | F | —(CH$_2$)$_3$— | O |
| H | OCH$_2$CH$_2$SCH$_3$ | Cl | H | F | —(CH$_2$)$_3$— | O |
| H | OCH$_2$CH$_2$SC$_2$H$_5$ | Cl | H | F | —(CH$_2$)$_3$— | O |
| H | SCH$_2$COOCH$_3$ | Cl | H | F | —(CH$_2$)$_3$— | O |
| H | SCH$_2$COOC$_2$H$_5$ | Cl | H | F | —(CH$_2$)$_3$— | O |
| H | SCH$_2$COOCH(CH$_3$)$_2$ | Cl | H | F | —(CH$_2$)$_3$— | O |
| H | SCH$_2$COOC$_4$H$_9$ | Cl | H | F | —(CH$_2$)$_3$— | O |
| H | SCH$_2$COOC$_5$H$_{11}$ | Cl | H | F | —(CH$_2$)$_3$— | O |
| H | SCH$_2$COO—⟨cyclopentyl⟩ | Cl | H | F | —(CH$_2$)$_3$— | O |
| H | SCH$_2$COOCH$_2$—⟨cyclopentyl⟩ | Cl | H | F | —(CH$_2$)$_3$— | O |
| H | SCH(CH$_3$)$_2$ | Cl | H | F | —(CH$_2$)$_3$— | O |
| H | SC$_4$H$_9$ | Cl | H | F | —(CH$_2$)$_3$— | O |
| H | SCH$_2$CH=CH$_2$ | Cl | H | F | —(CH$_2$)$_3$— | O |
| H | SCH$_2$C≡CH | Cl | H | F | —(CH$_2$)$_3$— | O |
| H | OCH$_2$COOCH$_2$CH=CH$_2$ | Cl | H | F | —(CH$_2$)$_3$— | O |
| H | OCH$_2$COOCH$_2$C≡CH | Cl | H | F | —(CH$_2$)$_3$— | O |
| H | SCH$_2$COOCH$_2$CH=CH$_2$ | Cl | H | F | —(CH$_2$)$_3$— | O |
| H | SCH$_2$COOCH$_2$C≡CH | Cl | H | F | —(CH$_2$)$_3$— | O |
| H | OCH$_2$CH=NOCH$_3$ | Cl | H | F | —(CH$_2$)$_3$— | O |
| H | OCH$_2$CH=NOCH$_2$CH=CH$_2$ | Cl | H | F | —(CH$_2$)$_3$— | O |
| H | OCH$_2$CH=NOCH$_2$COOCH$_3$ | Cl | H | F | —(CH$_2$)$_3$— | O |
| H | OCH$_2$COOCH$_2$COOCH$_3$ | Cl | H | F | —(CH$_2$)$_3$— | O |
| H | OCF$_2$CHFCl | Cl | H | F | —(CH$_2$)$_3$— | O |
| H | OCF$_2$CHF$_2$ | Cl | H | F | —(CH$_2$)$_4$— | O |
| H | OCH$_2$CH=CHCl | Cl | H | F | —(CH$_2$)$_3$— | O |
| H | OCF$_3$ | Cl | H | F | —(CH$_2$)$_3$— | O |
| H | OCF$_2$Cl | Cl | H | F | —(CH$_2$)$_3$— | O |

TABLE 1-continued

Examples of the compounds of the formula (I) or (IA) according to the invention

| R¹ | R² | R³ | R⁴ | R⁵ | R⁶ | R⁷ | Q |
|---|---|---|---|---|---|---|---|
| H | −N(CH₂CH=CH₂)−CO−CH₂−O− | | H | H | | −(CH₂)₃− | O |
| H | −N(CH₂CH=CH₂)−CO−CH₂−O− | | H | F | | −(CH₂)₃− | O |
| H | −N(CH₂C≡CH)−CO−CH₂−O− | | H | H | | −(CH₂)₃− | O |
| H | −N(CH₂C≡CH)−CO−CH₂−O− | | H | F | | −(CH₂)₃− | O |
| H | OCH₃ | CH₃ | H | F | | −(CH₂)₃− | O |
| H | OCH₂CH=CH₂ | CH₃ | H | F | | −(CH₂)₃− | O |
| H | OCH₂C≡CH | CH₃ | H | F | | −(CH₂)₃− | O |
| H | OCH₂COOCH₃ | CH₃ | H | F | | −(CH₂)₃− | O |
| H | OCH₃ | CN | H | F | | −(CH₂)₃− | O |
| H | OCH₂CH=CH₂ | CN | H | F | | −(CH₂)₃− | O |
| H | OCH₂C≡CH | CN | H | F | | −(CH₂)₃− | O |
| H | OCH₂COOCH₃ | CN | H | F | | −(CH₂)₃− | O |
| H | OCH₂CH₂OCH₃ | CN | H | F | | −(CH₂)₃− | O |
| H | OCHF₂ | CN | H | F | | −(CH₂)₄− | O |
| H | OCF₂CHFCl | CN | H | F | | −(CH₂)₃− | O |
| H | OCH₂CH=NOCH₃ | CN | H | F | | −(CH₂)₃− | O |
| H | OC₄H₉ | CN | H | F | | −(CH₂)₃− | O |
| H | CF₃ | Cl | H | F | | −(CH₂)₃− | O |
| H | CHF₂ | Cl | H | F | | −(CH₂)₃− | O |
| H | CF₂Cl | Cl | H | F | | −(CH₂)₃− | O |
| H | OCH₃ | Cl | H | F | CH₃ | Cl | O |
| H | OCH₃ | Cl | H | F | Cl | CH₃ | O |
| H | OCH₃ | Cl | H | F | Cl | H | O |
| H | OCH₃ | Cl | H | F | CH₃ | Br | O |
| H | OCH₃ | Cl | H | F | Br | CH₃ | O |
| H | OCH₃ | Cl | H | F | −CH₂−C(CH₃)₂−CH₂− | | O |
| H | OCH₃ | Cl | H | F | CH₃ | CH₃ | O |
| H | −NH−CO−CH₂−O− | | H | H | CH₃ | Cl | O |
| H | −NH−CO−CH₂−O− | | H | H | Cl | CH₃ | O |
| H | −NH−CO−CH₂−O− | | H | H | −CH₂−C(CH₃)₂−CH₂− | | O |
| H | −NH−CO−CH₂−O− | | H | H | −CH₂−CH(CH₃)−CH₂− | | O |
| H | Cl | Cl | H | Cl | CH₃ | CH₃ | O |
| H | Cl | Cl | H | F | CH₃ | CH₃ | O |
| H | Cl | CF₃ | H | Cl | | −(CH₂)₃− | O |
| H | Cl | Br | H | Cl | | −(CH₂)₃− | O |
| H | F | F | H | Cl | | −(CH₂)₃− | O |
| H | −N(CH₂CH=CH₂)−CO−CH₂−O− | | H | H | −CH₂−C(CH₃)₂−CH₂− | | O |
| H | −N(CH₂C≡CH)−CO−CH₂−O− | | H | F | −CH₂−C(CH₃)₂−CH₂− | | O |
| H | −N(CH₂CH=CH₂)−CO−CH₂−O− | | H | F | −CH₂−C(CH₃)₂−CH₂− | | O |
| H | −N(CH₂C≡CH)−CO−CH₂−O− | | H | H | −CH₂−C(CH₃)₂−CH₂− | | O |
| H | −N(CH₂-3-pyridyl)−CO−CH₂−O− | | H | H | CH₃ | H | O |

TABLE 1-continued

Examples of the compounds of the formula (I) or (IA) according to the invention

| R¹ | R² | R³ | R⁴ | R⁵ | R⁶ | R⁷ | Q |
|---|---|---|---|---|---|---|---|
| H | −N−CO−CH₂−O−<br>　│<br>　CH₂−(3-pyridyl) | | H | H | CH₃ | CH₃ | O |
| H | −N−CO−CH₂−O−<br>　│<br>　CH₂−(3-pyridyl) | | H | F | CH₃ | H | O |
| H | −N−CO−CH₂−O−<br>　│<br>　CH₂−(3-pyridyl) | | H | F | CH₃ | CH₃ | O |
| H | −N−CO−CH₂−O−<br>　│<br>　CH₂−(3-pyridyl) | | H | H | −(CH₂)₃− | | O |
| H | −N−CO−CH₂−O−<br>　│<br>　CH₂−(3-pyridyl) | | H | H | −CH₂−C(CH₃)₂−CH₂− | | O |
| H | −N−CO−CH₂−O−<br>　│<br>　CH₂−(3-pyridyl) | | H | F | −(CH₂)₃− | | O |
| H | −N−CO−CH₂−O−<br>　│<br>　CH₂−(3-pyridyl) | | H | F | −CH₂−C(CH₃)₂−CH₂− | | O |
| H | −N−CO−CH₂−O−<br>　│<br>　CH₂−(3-pyridyl) | | H | H | −(CH₂)₄− | | O |
| H | −N−CO−CH₂−O−<br>　│<br>　CH₂−(3-pyridyl) | | H | F | −(CH₂)₄− | | O |
| H | −N−CO−CH₂−O−<br>　│<br>　CH₂CH=CH₂ | | H | H | −(CH₂)₄− | | O |

TABLE 1-continued

Examples of the compounds of the formula (I) or (IA) according to the invention

| R$^1$ | R$^2$ | R$^3$ | R$^4$ | R$^5$ | R$^6$ | R$^7$ | Q |
|---|---|---|---|---|---|---|---|
| H | −N−CO−CH$_2$−O−<br>  |<br>  CH$_2$CH=CH$_2$ | | H | H | CH$_3$ | CH$_3$ | O |
| H | −N−CO−CH$_2$−O−<br>  |<br>  CH$_2$CH=CH$_2$ | | H | F | | −(CH$_2$)$_4$− | O |
| H | −N−CO−CH$_2$−O−<br>  |<br>  CH$_2$CH=CH$_2$ | | H | H | CH$_3$ | CH$_3$ | O |
| H | −N−CO−CH$_2$−O−<br>  |<br>  CH$_2$C≡CH | | H | H | | −(CH$_2$)$_4$− | O |
| H | −N−CO−CH$_2$−O−<br>  |<br>  CH$_2$C≡CH | | H | H | CH$_3$ | CH$_3$ | O |
| H | −N−CO−CH$_2$−O−<br>  |<br>  CH$_2$C≡CH | | H | F | | −(CH$_2$)$_4$− | O |
| H | −N−CO−CH$_2$−O−<br>  |<br>  CH$_2$C≡CH | | H | F | CH$_3$ | CH$_3$ | O |
| H | −N−CO−CH$_2$−O−<br>  |<br>  CH$_2$CH=CH$_2$ | | H | H | Br | CH$_3$ | O |
| H | −N−CO−CH$_2$−O−<br>  |<br>  CH$_2$CH−CH$_2$ | | H | F | Br | CH$_3$ | O |
| H | −N−CO−CH$_2$−O−<br>  |<br>  CH$_2$C≡CH | | H | H | Br | CH$_3$ | O |
| H | −N−CO−CH$_2$−O−<br>  |<br>  CH$_2$C≡CH | | H | F | Br | CH$_3$ | O |
| H | −N−CO−CH$_2$−O−<br>  |<br>  CH$_2$−(3-pyridyl) | | H | H | Br | CH$_3$ | O |
| H | −N−CO−CH$_2$−O−<br>  |<br>  CH$_2$−(3-pyridyl) | | H | F | Br | CH$_3$ | O |
| H | OCH−COOC$_2$H$_5$<br>  |<br>  CH$_3$ | CH$_3$ | H | F | CH$_3$ | H | O |
| H | OCH−COOC$_2$H$_5$<br>  |<br>  CH$_3$ | CH$_3$ | H | F | CH$_3$ | CH$_3$ | O |
| H | OCH−COOC$_2$H$_5$<br>  |<br>  CH$_3$ | CH$_3$ | H | F | | −(CH$_2$)$_3$− | O |
| H | OCH−COOC$_2$H$_5$<br>  |<br>  CH$_3$ | CH$_3$ | H | F | | −(CH$_2$)$_4$− | O |

TABLE 1-continued

Examples of the compounds of the formula (I) or (IA) according to the invention

| R¹ | R² | R³ | R⁴ | R⁵ | R⁶ | R⁷ | Q |
|---|---|---|---|---|---|---|---|
| H | OCH(CH₃)₂ | CH₃ | H | F | CH₃ | CH₃ | O |
| H | OCH(CH₃)₂ | CH₃ | H | F |  | —(CH₂)₃— | O |
| H | OCH(CH₃)₂ | CH₃ | H | F |  | —(CH₂)₄— | O |
| H | OCH₂C≡CH | CH₃ | H | F | CH₃ | CH₃ | O |
| H | OCH₂C≡CH | CH₃ | H | F |  | —(CH₂)₃— | O |
| H | OCH₂C≡CH | CH₃ | H | F |  | —(CH₂)₄— | O |
| H | OCH₂CH=CH₂ | CH₃ | H | F | CH₃ | CH₃ | O |
| H | OCH₂CH=CH₂ | CH₃ | H | F |  | —(CH₂)₃— | O |
| H | OCH₂CH=CH₂ | CH₃ | H | F |  | —(CH₂)₄— | O |
| H | OCH₂COO-cyclopentyl | CH₃ | H | F | CH₃ | CH₃ | O |
| H | OCH₂COO-cyclopentyl | CH₃ | H | F |  | —(CH₂)₃— | O |
| H | OCH₂COO-cyclopentyl | CH₃ | H | F |  | —(CH₂)₄— | O |
| H | SCH₂COO-cyclopentyl | CH₃ | H | F | CH₃ | CH₃ | O |
| H | SCH₂COO-cyclopentyl | CH₃ | H | F |  | —(CH₂)₃— | O |
| H | SCH₂COO-cyclopentyl | CH₃ | H | F |  | —(CH₂)₄— | O |
| H | OCH₂C≡CH | CN | H | H | CH₃ | CH₃ | O |
| H | OCH₂C≡CH | CN | H | F | CH₃ | CH₃ | O |
| H | OCH₂C≡CH | CN | H | H |  | —(CH₂)₄— | O |
| H | OCH₂C≡CH | CN | H | F |  | —(CH₂)₄— | O |
| H | OCH₂CH=CH₂ | CN | H | H | CH₃ | CH₃ | O |
| H | OCH₂CH=CH₂ | CN | H | F | CH₃ | CH₃ | O |
| H | OCH₂CH=CH₂ | CN | H | H |  | —(CH₂)₄— | O |
| H | OCH₂CH=CH₂ | CN | H | F |  | —(CH₂)₄— | O |
| H | (OCH₂CH₂)₂OC₂H₅ | CN | H | H | CH₃ | H | O |
| H | (OCH₂CH₂)₂OC₂H₅ | CN | H | F | CH₃ | H | O |
| H | (OCH₂CH₂)₂OC₂H₅ | CN | H | H | CH₃ | CH₃ | O |
| H | (OCH₂CH₂)₂OC₂H₅ | CN | H | F | CH₃ | CH₃ | O |
| H | (OCH₂CH₂)₂OC₂H₅ | CN | H | H |  | —(CH₂)₃— | O |
| H | (OCH₂CH₂)₂OC₂H₅ | CN | H | F |  | —(CH₂)₃— | O |
| H | (OCH₂CH₂)₂OC₂H₅ | CN | H | H |  | —(CH₂)₄— | O |
| H | (OCH₂CH₂)₂OC₂H₅ | CN | H | F |  | —(CH₂)₄— | O |
| H | SCH(CH₃)₂ | CN | H | F | CH₃ | H | O |
| H | SCH(CH₃)₂ | CN | H | F | CH₃ | CH₃ | O |
| H | SCH(CH₃)₂ | CN | H | F |  | —(CH₂)₃— | O |
| H | SCH(CH₃)₂ | CN | H | F |  | —(CH₂)₄— | O |
| H | SCH₂CH=CH₂ | CN | H | F | CH₃ | H | O |
| H | SCH₂CH=CH₂ | CN | H | F | CH₃ | CH₃ | O |
| H | SCH₂CH=CH₂ | CN | H | F |  | —(CH₂)₃— | O |
| H | SCH₂CH=CH₂ | CN | H | F |  | —(CH₂)₄— | O |
| H | —NH—CO—O— | H | H | CH₃ | H |  | O |

TABLE 1-continued

Examples of the compounds of the formula (I) or (IA) according to the invention

| R¹ | R² | | R³ | R⁴ | R⁵ | R⁶ | R⁷ | Q |
|---|---|---|---|---|---|---|---|---|
| H | —N(H)—CO—O— | | | H | H | CH₃ | CH₃ | O |
| H | —N(H)—CO—O— | | | H | H | | —(CH₂)₃— | O |
| H | —N(H)—CO—O— | | | H | H | | —(CH₂)₄— | O |
| H | —N(H)—CO—O— | | | H | F | CH₃ | H | O |
| H | —N(H)—CO—O— | | | H | F | CH₃ | CH₃ | O |
| H | —N(H)—CO—O— | | | H | F | | —(CH₂)₃— | O |
| H | —N(H)—CO—O— | | | H | F | | —(CH₂)₄— | O |
| H | —N(CH₂C≡CH)—CO—O— | | | H | H | CH₃ | H | O |
| H | —N(CH₂C≡CH)—CO—O— | | | H | H | CH₃ | CH₃ | O |
| H | —N(CH₂C≡CH)—CO—O— | | | H | H | | —(CH₂)₃— | O |
| H | —N(CH₂C≡CH)—CO—O— | | | H | H | | —(CH₂)₄— | O |
| H | —N(CH₂C≡CH)—CO—O— | | | H | F | CH₃ | H | O |
| H | —N(CH₂C≡CH)—CO—O— | | | H | F | CH₃ | CH₃ | O |
| H | —N(CH₂C≡CH)—CO—O— | | | H | F | | —(CH₂)₃— | O |
| H | —N(CH₂C≡CH)—CO—O— | | | H | F | | —(CH₂)₄— | O |
| H | —N(CH₂CH=CH₂)—CO—O— | | | H | H | CH₃ | H | O |
| H | —N(CH₂CH=CH₂)—CO—O— | | | H | H | CH₃ | CH₃ | O |
| H | —N(CH₂CH=CH₂)—CO—O— | | | H | H | | —(CH₂)₃— | O |
| H | —N(CH₂CH=CH₂)—CO—O— | | | H | H | | —(CH₂)₄— | O |

TABLE 1-continued

Examples of the compounds of the formula (I) or (IA) according to the invention

| R¹ | R² | R³ | R⁴ | R⁵ | R⁶ | R⁷ | Q |
|---|---|---|---|---|---|---|---|
| H | —N—CO—O—<br>    \|<br>    CH₂CH=CH₂ | H | F | CH₃ | | H | O |
| H | —N—CO—O—<br>    \|<br>    CH₂CH=CH₂ | H | F | CH₃ | | CH₃ | O |
| H | —N—CO—O—<br>    \|<br>    CH₂CH=CH₂ | H | F | | | —(CH₂)₃— | O |
| H | —N—CO—O—<br>    \|<br>    CH₂CH=CH₂ | H | F | | | —(CH₂)₄— | O |
| H | —N—CO—S—<br>    \|<br>    H | H | H | CH₃ | | H | O |
| H | —N—CO—S—<br>    \|<br>    H | H | H | CH₃ | | CH₃ | O |
| H | —N—CO—S—<br>    \|<br>    H | H | H | | | —(CH₂)₃— | O |
| H | —N—CO—S—<br>    \|<br>    H | H | H | | | —(CH₂)₄— | O |
| H | —N—CO—S—<br>    \|<br>    H | H | F | CH₃ | | H | O |
| H | —N—CO—S—<br>    \|<br>    H | H | F | CH₃ | | CH₃ | O |
| H | —N—CO—S—<br>    \|<br>    H | H | F | | | —(CH₂)₃— | O |
| H | —N—CO—S—<br>    \|<br>    H | H | F | | | —(CH₂)₄— | O |
| H | —N—CO—S—<br>    \|<br>    CH₂C≡CH | H | H | CH₃ | | H | O |
| H | —N—CO—S—<br>    \|<br>    CH₂C≡CH | H | H | CH₃ | | CH₃ | O |
| H | —N—CO—S—<br>    \|<br>    CH₂C≡CH | H | H | | | —(CH₂)₃— | O |
| H | —N—CO—S—<br>    \|<br>    CH₂C≡CH | H | H | | | —(CH₂)₄— | O |
| H | —N—CO—S—<br>    \|<br>    CH₂C≡CH | H | F | CH₃ | | H | O |
| H | —N—CO—S—<br>    \|<br>    CH₂C≡CH | H | F | CH₃ | | CH₃ | O |
| H | —N—CO—S—<br>    \|<br>    CH₂C≡CH | H | F | | | —(CH₂)₃— | O |

TABLE 1-continued

Examples of the compounds of the formula (I) or (IA) according to the invention

| R¹ | R² | R³ | R⁴ | R⁵ | R⁶ | R⁷ | Q |
|---|---|---|---|---|---|---|---|
| H | —N(CH₂C≡CH)—CO—S— | | H | F | | —(CH₂)₄— | O |
| H | —N(CH₂CH=CH₂)—CO—S— | | H | H | CH₃ | H | O |
| H | —N(CH₂CH=CH₂)—CO—S— | | H | H | CH₃ | CH₃ | O |
| H | —N(CH₂CH=CH₂)—CO—S— | | H | H | | —(CH₂)₃— | O |
| H | —N(CH₂CH=CH₂)—CO—S— | | H | H | | —(CH₂)₄— | O |
| H | —N(CH₂CH=CH₂)—CO—S— | | H | F | CH₃ | H | O |
| H | —N(CH₂CH=CH₂)—CO—S— | | H | F | CH₃ | CH₃ | O |
| H | —N(CH₂CH=CH₂)—CO—S— | | H | F | | —(CH₂)₃— | O |
| H | —N(CH₂CH=CH₂)—CO—S— | | H | F | | —(CH₂)₄— | O |

If, for example, 2-fluoro-4-methyl-5-propargyloxy-phenyl isocyanate and 2,2,6-trimethyl-1,3-dioxin-4-one are used as starting substances in process (a) according to the invention, the course of the reaction can be represented by the following equation:

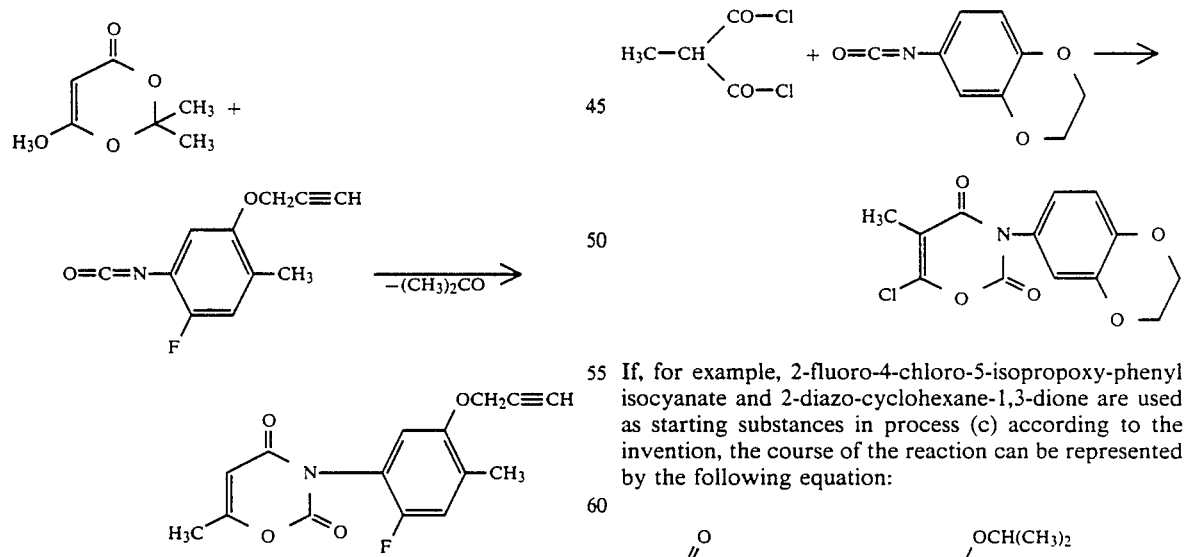

If, for example, methylmalonyl dichloride and 6-isocyanato-1,4-benzodioxane are used as starting substances in process (b) according to the invention, the course of the reaction can be represented by the following equation:

If, for example, 2-fluoro-4-chloro-5-isopropoxy-phenyl isocyanate and 2-diazo-cyclohexane-1,3-dione are used as starting substances in process (c) according to the invention, the course of the reaction can be represented by the following equation:

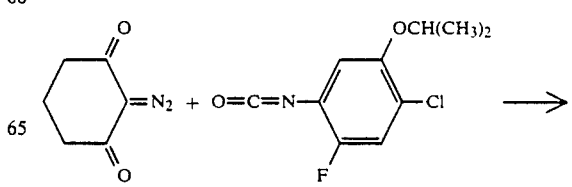

-continued

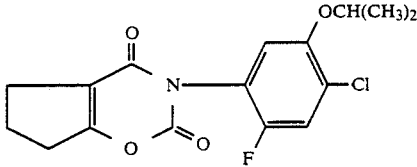

If, for example, 2-fluoro-4-chloro-5-propargyloxy-phenyl isocyanate and methyl salicylate are used as starting substances in process (d) according to the invention, the course of the reaction can be represented by the following equation:

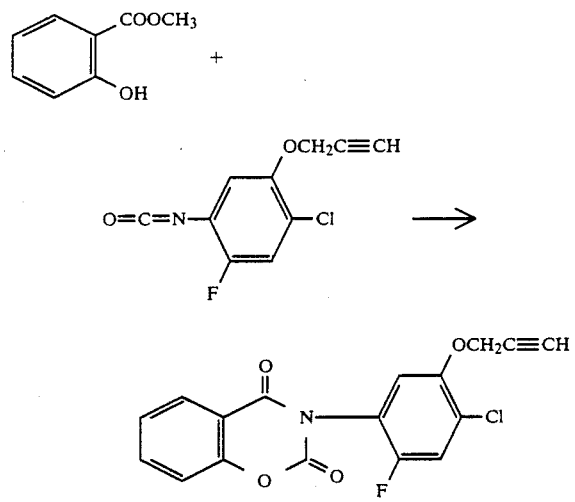

Formula (II) provides a general definition of the aryl iso(thio)cyanates required as starting substances in processes (a), (b), (c) and (d) according to the invention for the preparation of compounds of the formula (I).

In formula (II), $R^1$, $R^2$, $R^3$, $R^4$, $R^5$ and Q preferably, or in particular, have the same meanings as have already been mentioned in connection with the description of the compounds of the formula (I) according to the invention as being preferred, or particularly preferred.

Examples of the starting substances of the formula (II) which may be mentioned are: 2-fluoro-, 3-fluoro-, 4-fluoro- and 2,4-difluoro-phenyl isocyanate or -phenyl isothiocyanate, 2-chloro-, 3-chloro-, 4-chloro-, 2,3-dichloro-, 2,4- dichloro- and 3,4-dichloro-phenyl isocyanate or -phenyl isothiocyanate, 3-bromo- and 4-bromo-phenyl isocyanate or -phenylisothiocyanate, 3-trifluoromethyl- and 4-trifluromethyl-phenyl isocyanate or -phenyl isothiocyanate, 3-chloro-4-trifluromethyl- and 4-chloro-3-trifluoromethyl-phenyl isocyanate or -phenyl isothiocyanate, 3-chloro-4-methyl-and 4- chloro-3-methyl-phenyl isocyanate or -phenyl isothiocyanate, 3-methoxy-, 3-ethoxy-, 4-methoxy, 4-ethoxy- and 3-isopropoxy-phenyl isocyanate or -phenylisothiocyanate, 4-nitro-phenyl isocyanate and 4-nitro-phenyl isothiocyanate, 2,4-dichloro-5-methoxy-, 2,4-dichloro-5-ethoxy-and 2,4-dichloro-5-isopropoxy-phenyl isocyanate or -phenyl isothiocyanate, 2-fluoro-4-chloro-5-methoxycarbonylmethoxy-phenyl isocyanate or -phenyl isothiocyanate, 2,4-dichloro-5-methoxycarbonylmethoxy-phenyl isocyanate or -phenyl isothiocyanate, 3-methoxy-4-chlorophenyl isocyanate or -phenyl isothiocyanate, 3-isopropoxy-4-chloro-phenyl isocyanate or -phenyl isothiocyanate, 3-(1-methoxycarbonyl)-ethoxy-4-chlorophenylisocyanate or -phenyl isothiocyanate, 2,4-dichloro-5-(1-methoxycarbonyl)-ethoxy-phenyl isocyanate or -phenyl isothiocyanate, 3-allyloxy-4-chloro-phenyl isocyanate or -phenyl isothiocanate, 2-fluoro-4-chloro-5-allyloxy-phenyl isocyanate or -phenyl isothiocyanate, 2,4-dichloro-5-allyloxy-phenyl isocyanate or -phenyl isothiocyanate, 3-propargyloxy-4-chloro-phenyl isocyanate or -phenyl isothiocyanate, 2,4-dichloro-5-propargyloxy-phenyl isocyanate or -phenyl isothiocyanate, 2-fluoro-4-chloro-5-propargyloxy-phenyl isocyanate or -phenyl isothiocyanate.

Some of the starting substances of the formula (II) are known and can be prepared by processes known per se (cf. EP-A 70,389, EP-A 69,855, EP-A 75,267, EP-A 230,874, EP-A 255,601, EP-A 263 299).

The aryl iso(thio)cyanates of the formula (II) are obtained when arylamines of the general formula (X)

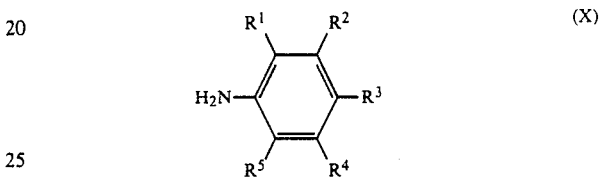

in which
$R^1$, $R^2$, $R^3$, $R^4$ and $R^5$ have the abovementioned meanings, are reacted with phosgene or with thiophosgene, if example, toluene or chloroform and water, at temperatures between $-10°$ C. and 120° C.

The arylamines of the general formula (X) are known and/or can be prepared by processes known per se (cf. EP-A 61,741, EP-A 69,855, EP-A 70,389, EP-A 75,267, EP-A 83,055, EP-A 95,192, EP-A 170,191, EP-A 211,805, EPA 218,972, EP-A 237,899, DE-OS (German Published Specification) 2,740,836).

Formula (III) provides a general definition of the 1,3-dioxin-4-ones also to be used as starting substances in process (a) according to the invention for the preparation of compounds of the formula (I).

In formula III), $R^6$ and $R^7$ preferably, or in particular, have those meanings which have already been mentioned above in connection with the description of the compounds of the formula (I) according to the invention as being preferred, or particularly preferred, for $R^6$ and $R^7$, and $R^9$ and $R^{10}$ preferably represent hydrogen or $C_1$-$C_6$-alkyl, in particular methyl.

Examples of the starting substances of the formula (III) are listed in Table 2 below:

TABLE 2

Examples of the starting substances of the formula (III)

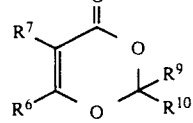
(III)

| $R^6$ | $R^7$ | $R^9$ | $R^{10}$ |
|---|---|---|---|
| $CH_3$ | H | $CH_3$ | $CH_3$ |
| | $-(CH_2)_3-$ | $CH_3$ | $CH_3$ |
| | $-(CH_2)_4-$ | $CH_3$ | $CH_3$ |
| | $-CH_2-C(CH_3)_2-CH_2-$ | $CH_3$ | $CH_3$ |
| $CH_3$ | H | H | $C_2H_5$ |
| $CH_3$ | H | H | $C_3H_7$ |
| $CH_3$ | H | $CH_3$ | $C_2H_5$ |

TABLE 2-continued

Examples of the starting substances of the formula (III)

$$\underset{R^6}{\overset{R^7}{>}}=\underset{O}{\overset{O}{\underset{\|}{C}}}\underset{O}{\overset{R^9}{\underset{R^{10}}{<}}}  \quad (III)$$

| $R^6$ | $R^7$ | $R^9$ | $R^{10}$ |
|---|---|---|---|
|  | —(CH$_2$)$_3$— | CH$_3$ | C$_2$H$_5$ |
| CH$_3$ | CH$_3$ | CH$_3$ | CH$_3$ |
|  | —CH$_2$—C(CH$_3$)$_2$—CH— | CH$_3$ | CH$_3$ |
| CH$_3$ | C$_2$H$_5$ | CH$_3$ | CH$_3$ |

The starting substances of the formula (III) are known and/or can be prepared by processes known per se (cf. Chem. Ber. 105 (1972), 137–149; J. Am. Chem. Soc. 74 (1952), 6305–6306; loc. cit. 75 (1953), 5400–5402; DE-OS (German Published Specification) 1,957,312).

Formula (IV) provides a general definition of the dicarboxylic acid dichlorides to be used as starting substances in process (b) according to the invention for the preparation of compounds of the formula (I).

In formula (IV), $R^7$ preferably, or in particular, has the meaning which has already- been indicated above in connection with the description of the compounds of the formula (I) according to the invention as being preferred, or particularly preferred, for $R^7$.

Examples of the starting substances of the formula (IV) which may be mentioned are: malonyl dichloride, methylmalonyl dichloride and ethylmalonyl dichloride.

The dicarboxylic acid dichlorides of the formula (IV) are known chemicals for organic synthesis.

Formula (V) provides a general definition of the 2-diazo-1,3-diketones to be used as starting substances in process (c) according to the invention for the preparation of compounds of the formula (I).

In formula (V), $R^6$ and $R^7$ preferably, or in particular, have those meanings which have already been indicated above in connection with the description of the compounds of the formula (I) according to the invention as being preferred, or particularly preferred, for $R^6$ and $R^7$.

Examples of the starting substances of the formula (V) which may be mentioned are: 2-diazo-butane-1,3-dione, 3-diazo-pentane-2,4-dione, 3-diazo-hexane-2,4-dione, 2-diazo-cyclopentane-1,3-dione, 2-diazo-cyclohexane-1,3-dione, 2-diazo-cylcoheptane-1,3-dione and 2-diazo-5,5-dimethyl-cyclohexane-1,3-dione.

The starting substances of the formula (V) are known and/or can be prepared by processes which are known per se (cf. Liebigs Ann. Chem. 687 (1965), 214–231; Chem. Ber. 99 (1966), 3128–3147; loc. cit. 104 (1971), 1942–1956).

Formula (VI) provides a general definition of salicylic acid and the esters thereof, which are to be used as starting substances in process (d) according to the invention for the preparation of compounds of the formula (I).

In formula (VI), R preferably, or in particular, has the meaning which has already been indicated above in connection with the description of the compounds of the formula (I) according to the invention as being preferred, or particularly preferred, for R.

Examples of the starting substances of the formula (VI) which may be mentioned are: salicylic acid as well as the methyl ester and ethyl ester thereof.

The starting substances of the formula (VI) are known chemicals for organic synthesis.

If appropriate, process (a) according to the invention for the preparation of the novel compounds o the formula (I) is carried out using diluents. Suitable diluents are preferably high-boiling, inert organic solvents. These include, above all, optionally halogenated hydrocarbons, such as decalin, tetralin, toluene, xylene, furthermore chlorobenzene and 1,2-dichlorobenzene, and also mesitylene.

In process (a) according to the invention, the reaction temperatures can be varied within a relatively wide range. In general, the process is carried out at temperatures between 80° C. and 250° C., preferably at temperatures between 120° C. and 220° C.

Process (a) according to the invention is generally carried out under atmospheric pressure. However, it is also possible to carry out the process under increased or reduced pressure.

For carrying out process (a) according to the invention, the starting substances required in each case are generally employed in approximately equimolar amounts. However, it is also possible to use one of the two components employed in each case in relatively large excess. In general, the reactions are carried out in a suitable diluent—but, if appropriate, also without a diluent—and the reaction mixture is stirred at the temperature required in each case. Working-up in process (a) according to the invention is carried out in each case by customary methods (cf. also the Preparation Examples).

Process (b) according to the invention for the preparation of the novel compounds of the formula (I) is preferably carried out using diluents. Suitable diluents for this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

In process (b) according to the invention, the reaction temperatures can be varied within a relatively wide range. In general, the process is carried out at temperatures between 0° C. and 150° C., preferably at temperatures between 20° C. and 100° C.

Process (b) according to the invention is generally carried out under atmospheric pressure. However, it is also possible to carry out the process under increased or reduced pressure.

For carrying out process (b) according to the invention, the starting substances required in each case are generally employed in approximately equimolar amounts. However, it is also possible to use one of the two components employed in each case in relatively large excess. If appropriate, the reactions are carried out in a suitable diluent, and the reaction mixture is stirred for several hours at the temperature required in each case. Working-up in process (b) according to the invention is carried out in each case by customary methods.

If appropriate, process (c) according to the invention for the preparation of the novel compounds of the formula (I) is carried out using diluents. Suitable diluents are preferably the same inert organic solvents as have been indicated above in process (a).

In process (c) according to the invention, the reaction temperatures can be varied within a relatively wide range. In general, the process is carried out at temperatures between 80° C. and 250° C., preferably at temperatures between 120° C. and 220° C.

Process (c) according to the invention is generally carried out under atmospheric pressure. However, it is also possible to carry out the process under increased or reduced pressure.

For carrying out process (c) according to the invention, the starting substances required in each case are generally employed in approximately equimolar amounts. However, it is also possible to use one of the two components employed in each case in relatively large excess. If appropriate, the reactions are carried out in a suitable diluent, and the reaction mixture is stirred for several hours at the temperature required in each case. Working-up in process c) according to the invention is carried out in each case by customary methods (cf. also the Preparation Examples).

If appropriate, process (d) according to the invention for the preparation of the novel compounds of the formula (I) is carried out in the presence of a diluent. Suitable diluents are preferably the same inert organic solvents as have been indicated above in process (a)

Acid acceptors which can be employed in process (d) according to the invention are all acid-binding agents which can customarily be used for reactions of this type. Aliphatic, aromatic or heterocyclic amines, for example triethylamine, trimethylamine, dimethylaniline, dimethylbenzylamine, pyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO) are preferably suitable.

In process (d) according to the invention, the reaction temperatures can be varied within a relatively wide range. In general, the process is carried out at temperatures between 0° C. and 250° C., preferably at temperatures between 10° C. and 200° C.

In general, process (d) according to the invention is carried out under atmospheric pressure. However, it is also possible to carry out the process under increased or reduced pressure.

For carrying out process (d) according to the invention, the starting substances required in each case are generally employed in approximately equimolar amounts. However, it is also possible to use one of the two components employed in each case in relatively large excess. In general, the reactions are carried out in a suitable diluent in the presence of an acid acceptor, and the reaction mixture is stirred for several hours at the temperature required in each case. Working-up in process (d) according to the invention is carried out in each case by customary methods.

The active compounds according to the invention can be used as defoliants, desiccants, agents for destroying broadleaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the cenera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Apparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds according to the invention of the formula (I) are particularly suitable for selectively combating dicotyledon weeds in monocotyledon crops, especially using the post-emergence method.

To a certain extent, they also show a fungicidal action, for example against Phytophthora species.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as album n hydrolysis products; as dispersing agents there are suitable: for example ligninsulphite waste liquors and methylcellulose.

Adhesives, such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N,-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans, furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 2-chloro-4-ethylamino-6-isopropylamino-1,3,5-triazine (ATRAZIN); 3-isopropyl-2,1,3-benzothiadiazin-4-one 2,2-dioxide (BENTANONE); methyl 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)phenoxy)phenoxy]-propionic acid, its methyl ester or its ethyl ester (DICLOFOP); 4-amino-6-t-butyl-3-ethylthio-1,2,4-triazin-5(4H)-one ETHIOZIN); 2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methyl ester FLUROXYPYR]; methyl 2-[4,5-dihydro-4-methyl-4-(1-methylethyl)-5-oxo-1H-imidazol-2-yl]-4-(5)methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)acetic acid (MCPA); (4-chloro-2-methylphenoxy)-propionic acid (MCPP); N-methyl-2-(1,3-benzothiazol-2-yloxy)acetanilide (MEFENACET); N-(1-ethylpropyl)-3,4-dimethyl-2,6-dinitro-aniline (PENDIMETHALIN); 0-(6-chloro-3-phenylpyridazin-4-yl) S-octyl thiocarbonate (PYRIDATE); 4-ethylamino-2-t-butylamino-6-methylthio-s-triazine (TERBUTRYNE) and methyl 3-[[[[(4-methoxy-6-methyl-1,3,5-triazin-2-yl-)-amino]-carbonyl]-amino]-sulphonyl]-thiophene-2-carboxylate (THIAMETURON). Surprisingly, some mixtures also show synergistic action.

Mixtures with other known active compounds, such as fungicides, insecticides, acaricides, nematicides, bird repellents, plant nutrients and agents which improve the soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied both before and after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the examples which follow.

PREPARATION EXAMPLES

EXAMPLE 1

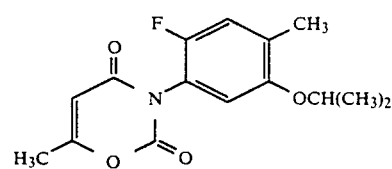

(Process (a))

A mixture of 1.42 g (0.01 mol) of 2,2,6-trimethyl-4H-1,3-dioxin-4-one and 2.09 g (0.01 mol) of 2-fluoro-4-methyl-5-isopropoxy-phenyl isocyanate is heated at 140° C. for 3 hours, in the course of which acetone distills over. After the mixture has cooled, the precipitate is filtered off.

0.7 g (23% of theory) of 3,4-dihydro-3-(2-fluoro-4-methyl-5-isopropoxy-phenyl)-6-methyl-2H-1,3benzine-2,4-dione of melting point 122° C.–124° C. are obtained.

¹H-NMR (80 Mhz, CDCl₃, δ): 7.01 (d, 1H, J=9.0 Hz); 6.66 (d, 1H, J=5.0 Hz), 4.40 (sept. 1H, J=5.9 Hz); 2.26 (s, 3H); 2.22 (s, 3H); 1.32 (d, 6H, J=5.8 Hz).

EXAMPLE 2

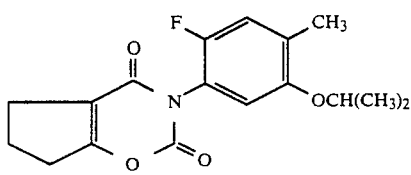

(Process (a))

A solution of 1.68 g (0.01 mol) of 6,7-dihydro-5H-cyclopenta-1,3-dioxin-4-one and 2.09 g (0.01 mol) of 2-fluoro-4-methyl-5-isopropoxyphenyl isocyanate in 5 ml of o-xylene is heated at 150° C. for one hour.

After the volatile component has been removed, 0.91 g (28.5% of theory) of 3-(2-fluoro-4-methyl-5-isopropoxyphenyl)-2,3,4,5,6,7-hexahydrocyclopenta[e]-1,3- oxazine-2,4-dione of melting point 131° C.–133° C. is isolated by column chromatography over silica gel.

¹H-NMR (80 Mhz, CDCl₃, δ): 7.01 (d, 1H, J=9.0 Hz) 6.65 (d, 1H, J=5.0 Hz); 4.39 (sept. 1H, J=5.8 Hz); 2.85 (m, 2H); 2.76 (m, 2H); 2.22 (s, 3H), 2.16 (m, 2H); 1.32 (d, 6H, J=5.6 Hz).

EXAMPLE 3

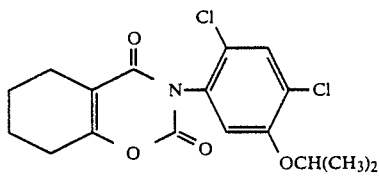

(Process (a))

A solution of 5 g (0.027 mol) of 2,2-dimethyl-4,5,6,7,8-hexahydro-cyclohexa-1,3-dioxin-4-one and 6.7 g (0.027 mol) of 2,4-dichloro-5-isopropyloxy-phenyl isocyanate in 20 ml of mesitylene is heated at 210° C. for 30 minutes. In this process, the mesitylene is distilled off.

Following purification by column chromatography on silica gel with the eluent petroleum ether:ethyl acetate 5:1, 2.1 g (21% of theory) of 2,3,4,5,6,7,8- heptahydro-3-(2,4-dichloro-5-isopropoxy-phenyl)-cyclohexa[e]-1,2-oxazin-2,4-dione are obtained as an oily residue.

¹H-NMR (200 Mhz CDCl₃, δ): 1.36 (d 6H); 1.68–1.95 and 2.38–2.55 (m, 8H); 4.50 (m, 1H); 6.84 (s, 1H); 7.53 (s, 1H).

EXAMPLE 4

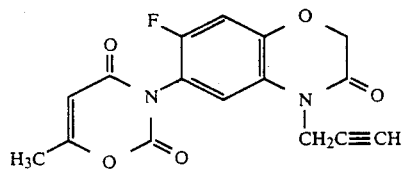

(Process (a))

2.84 g (0.02 mol) of 2,2,6-trimethyl-4H-1,3-dioxin-4-one are added dropwise to a solution, pre-heated at 150° C., of 4.92 g (0.02 mol) of 7-fluoro-6-isocyanato-4-propargyl-3,4-dihydro-3-oxo-2H-1,4-benzoxine in 10 ml of o-dichlorobenzene. The reaction mixture is heated at this temperature for 4 hours, cooled and evaporated. The residue is separated by column chromatography over silica gel.

1.68 g (25.5% of theory) of 3,4-dihydro-3-(7-fluoro-4-propargyl-3,4-dihydro-3-one-2H-1,4-benzoxazin- 6-yl)-6-methyl-2H-1,3-oxazine-2,4-dione of melting point 244°–248° C. are obtained.

¹H-NMR (80 Mhz, CDCl₃/DMSO, δ): 7.36 (d, 1H, J=6.6 Hz); 7.05 (d, 1H, J=9.0 Hz); 6.09 (s, 1H); 4.77 (s, 2H); 4.65 (d, 2H, J=2.0 Hz); 3.01 (t, 1H, J=2.0 Hz); 2.28 (s, 3H).

EXAMPLE 5

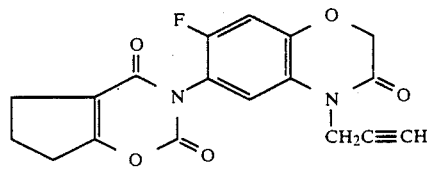

(Process (a))

3.36 g (0.02 mol) of 6,7-dihydro-5H-cyclopenta-1,3-dioxin-4-one and 4.92 g (0.02 mol) of 7-fluoro-6-isocyanato-4-propargyl-3,4-dihydro-3-oxo-2H-1,4-benzoxazine in 10 ml of o-dichlorobenzene are heated at 150° C. for 4 hours. After the mixture has cooled and evaporated, the residue is separated by column chromatography.

1.58 g (22.2% of theory) of 3-(7-fluoro-4-propargyl-3,4-dihydro-3-oxo-2H-1,4-benzoxazin-6-yl)-2,3,4,5,6,7-hexahydrocyclopenta[e]-1,3-oxazine-2,4-dione of melting point 222° C.–224° C. are isolated.

¹H-NMR (80 Mhz, CDCl₃, δ): 7.08 (d, 1H J=6.6 Hz); 6.90 (d, 1H, J=9.0 Hz); 4.70 (dd, 1H, J=17.3 Hz, J'=2.0 Hz); 4.6 g (s, 2H); 4.61 (dd, 1H, J=17.3 Hz, J'=2.0 Hz); 2.87 (m, 2H); 2.77 (m, 2H); 2.29 (t, 1H, J=2.0 Hz); 2.21 (m, 2H).

EXAMPLE 6

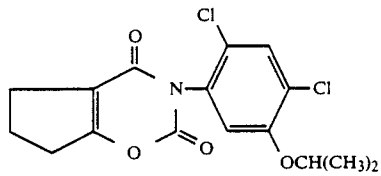

(Process (c))

A solution of 10 g (75 mmol) of 2-diazo-cyclohexa-1,3-dione and 18.3 g (75 mmol) of 2,4-dichloro-5-isopropoxy-phenyl isocyanate in 50 ml of xylene is added, dropwise at 140° C. to 5 ml of xylene. When the addition is complete, stirring is continued for 10 minutes at 140° C. The solvent is distilled off, and the residue is purified by column chromatography on silica gel using petroleum ether:methyl acetate 5:1.

16.8 g (63% of theory) of 2,3,4,5,6,7-hexahydro-3-[dichloro-5-isopropoxy-phenyl]-cyclopenta[e]-1,3-oxazine-2,4-dione are obtained.

$^1$H-NMR (200 Mhz, CDCl$_3$, δ): 1.38 (d, 6H); 2.10-2 25 and 2.65-2.90 (m, 6H); 4.50 (m, 1H); 6.83 (s, 1H); 7.52 (s, 1H).

EXAMPLE 7

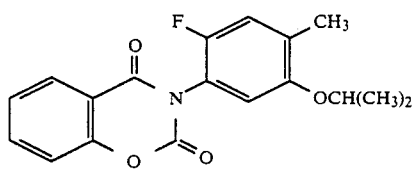

(Process (d))

2.76 g (0.02 mol) of salicylic acid are initially introduced in 20 ml of o-dichlorobenzene, 2.22 g (0.022 mol) of triethylamine are added dropwise to the mixture, and stirring is continued at room temperature for 30 minutes. 4.18 g (0.02 mol) of 2-fluoro-4-methyl-5-isopropoxy-phenyl isocyanate are subsequently added, and the mixture is heated at 150° C. for 4 hours.

Following evaporation and purification by column chromatography, 1.38 g (21% of theory) of 3-(2-fluoro-4-methyl-5-isopropoxyphenyl)-benzo[e]-1,3-oxazine-2,4-dione of melting point 118-122° C. are obtained.

$^1$H-NMR (80 Mhz, CDCl$_3$, δ): 8.14 (dd, 1H, J=8.0 Hz, J'=1.0 Hz); 7.75 (dt, 1H, J =8.0 Hz, J'=1.0 Hz); 7.41 (dt, 1H, J=8.0 Hz, J'=1.0 Hz); 7.35 (d, 1H, J=8.0 Hz); 7.05 (d, 1H, J=9.0 Hz); 6.74 (d, 1H, J=5.0 Hz); 4.42 (sept., 1H, J=5.8 Hz); 2.25 (s, 3H); 1.33 (d, 6H, J=5.8 Hz).

The compounds of the formula (I) listed in Table below can be prepared analogously to Examples 1 to 7 and in accordance with the general description of the preparation processes according to the invention.

TABLE 3

Preparation examples of the compounds of the formula (I)

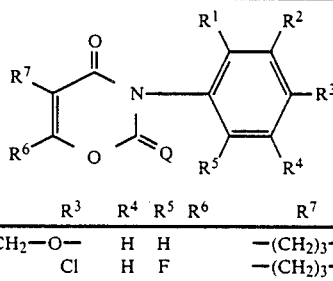

(I)

| Ex. No. | R$^1$ | R$^2$ | R$^3$ | R$^4$ | R$^5$ | R$^6$ | R$^7$ | Q | Physical data |
|---|---|---|---|---|---|---|---|---|---|
| 8 | H | —O—CH$_2$CH$_2$—O— | | H | H | | —(CH$_2$)$_3$— | O | mp. 203° C. |
| 9 | H | OCH$_2$C≡CH | Cl | H | F | | —(CH$_2$)$_3$— | O | mp. 131° C. |
| 10 | H | —N—CO—CH$_2$—O—<br>｜<br>CH$_2$C≡CH | | H | F | —CH=CH—CH=CH— | | O | (a) |
| 11 | H | OCF$_2$Cl | Cl | H | F | | —(CH$_2$)$_3$— | O | (b) |
| 12 | H | OCF$_2$CHFCl | Cl | H | F | | —(CH$_2$)$_4$— | O | (c) |
| 13 | H | —O—CF$_2$—O— | | H | H | | —(CH$_2$)$_3$— | O | mp. 198° C. |
| 14 | H | —O—CF$_2$—CHF—O— | | H | F | | —(CH$_2$)$_3$— | O | |
| 15 | H | —O—CHF—CF$_2$—O— | | H | F | | —(CH$_2$)$_3$— | O | |
| 16 | H | —O—CH$_2$—O—CH$_2$— | | H | H | | —(CH$_2$)$_3$— | O | mp. 172° C. |
| 17 | H | —N—CO—CH$_2$—O—<br>｜<br>CH$_2$C≡CH | | H | F | | —(CH$_2$)$_4$— | O | |
| 18 | H | OCF$_2$Cl | Cl | H | F | | —(CH$_2$)$_4$— | O | |
| 19 | H | OCH$_2$C≡CH | CH$_3$ | H | F | | —(CH$_2$)$_4$— | O | |
| 20 | H | —N—CO—CH$_2$—O—<br>｜<br>CH$_2$OCH$_3$ | | H | H | | —(CH$_2$)$_4$— | O | |
| 21 | H | —N—CO—CH$_2$—O—<br>｜<br>CH$_2$C=CH$_2$<br>｜<br>Cl | | H | H | CH$_3$ | CH$_3$ | O | |
| 22 | H | OCH$_2$≡CH | Cl | H | F | | —(CH$_2$)$_4$— | O | |
| 23 | H | —N—CO—CH$_2$—O—<br>｜<br>CH$_2$OCH$_3$ | | H | F | | —(CH$_2$)$_4$— | O | |

TABLE 3-continued

Preparation examples of the compounds of the formula (I)

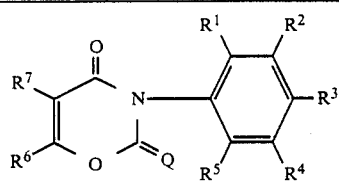

(I)

| Ex. No. | R¹ | R² | R³ | R⁴ | R⁵ | R⁶ | R⁷ | Q | Physical data |
|---|---|---|---|---|---|---|---|---|---|
| 24 | H | OCH$_2$CH=CH$_2$ | CN | H | | F | —(CH$_2$)$_4$— | O | |
| 25 | H | —N(CH$_2$OCH$_3$)—CO—CH$_2$—O— | | H | | H | —(CH$_2$)$_3$— | O | |
| 26 | H | OCH$_2$C≡CH | Cl | H | F | CH$_3$ | CH$_3$ | O | |
| 27 | H | —N(CH$_2$OCH$_3$)—CO—CH$_2$—O— | | H | | F | —(CH$_2$)$_3$— | O | mp. 184° C. |
| 28 | H | OCH$_2$CH=CH$_2$ | CN | H | | F | —(CH$_2$)$_3$— | O | |
| 29 | H | —N(CH$_2$C≡CH)—CO—CH$_2$—O— | | H | | H | —(CH$_2$)$_4$— | S | |
| 30 | H | —N(CH$_2$-2-pyridyl)—CO—CH$_2$—O— | | H | | F | —(CH$_2$)$_4$— | O | mp. 212° C. |
| 31 | H | —N(CH$_2$COOC$_2$H$_5$)—CO—CH$_2$—O— | | H | | H | —(CH$_2$)$_3$— | O | mp. 224° C. |
| 32 | H | —N(CH$_2$COOC$_2$H$_5$)—CO—CH$_2$—O— | | H | | H | —(CH$_2$)$_4$— | O | mp. 221° C. |
| 33 | H | —N(CH$_2$CN)—CO—CH$_2$—O— | | H | | H | —(CH$_2$)$_4$— | O | |
| 34 | H | —N(CH$_2$CN)—CO—CH$_2$—O— | | H | | H | —(CH$_2$)$_3$— | O | |
| 35 | H | —N(CH$_2$CH$_2$OC$_2$H$_5$)—CO—CH$_2$—O— | | H | | H | —(CH$_2$)$_3$ | O | |
| 36 | H | —N(CH$_2$CH$_2$OC$_2$H$_5$)—CO—CH$_2$—O— | | H | | H | —(CH$_2$)$_4$ | O | |
| 37 | H | —N(CH$_2$OCH$_3$)—CO—CH$_2$—O— | | H | F | CH$_3$ | CH$_3$ | O | |
| 38 | H | F | CN | H | | F | —(CH$_2$)$_4$— | O | mp. 159-161° C. |
| 39 | H | F | CN | H | F | CH$_3$ | CH$_3$ | O | mp. 235° C. |
| 40 | H | —N(CH$_2$CN)—CO—CH$_2$—O— | | H | | F | —(CH$_2$)$_4$— | O | mp. 220° C. |
| 41 | H | —N(CH$_2$CN)—CO—CH$_2$—O— | | H | | F | —(CH$_2$)$_3$— | O | mp. 209-211° C. |

TABLE 3-continued

Preparation examples of the compounds of the formula (I)

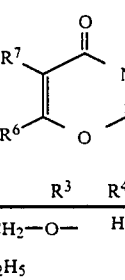

| Ex. No. | R¹ | R² | R³ | R⁴ | R⁵ | R⁶ | R⁷ | Q | Physical data |
|---|---|---|---|---|---|---|---|---|---|
| 42 | H | —N—CO—CH₂—O—<br>   \|<br>   CH₂COOC₂H₅ | | H | F | | —(CH₂)₄— | O | ¹H-NMR (CDCl₃)<br>δ = 1,25(3H);<br>1,80(4H);<br>2,45(4H) |
| 43 | H | —N—CO—CH₂—O—<br>   \|<br>   CH₂COOC₂H₅ | | H | F | | —(CH₂)₃— | O | MS: [M⁺] 404,<br>294, 221 |
| 44 | H | —N—CO—O— | | H | F | | —(CH₂)₄— | O | MS: [M⁺] 362, 238 |
| 45 | H | —N—CO—O—<br>   \|<br>   CH₂C≡CH | | H | F | | —(CH₂)₄ | O | MS: [M⁺] 356,<br>330, 232 |
| 46 | H | —N—CO—O—<br>   \|<br>   CH₂C≡CH | | H | H | | —(CH₂)₄ | O | ¹H-NMR (CDCl₃):<br>δ = 1.80(4);<br>2.45(4); 4.60(2);<br>7.1–7,3(3) |
| 47 | H | —N—CO—CH₂—O—<br>   \|<br>   CH₂CN | | H | F | CH₃ | CH₃ | O | mp. 189° C. |
| 48 | H | —N—CO—CH₂—O—<br>   \|<br>   CH₂COOC₂H₅ | | H | F | CH₃ | CH₃ | O | ¹H-NMR (CDCl₃):<br>δ = 1.25(3H);<br>1.95(3), 2.28(3);<br>4.20(2), 4.60(2) |
| 49 | H | —N—CO—O—<br>   \|<br>   CH₂OCH₃ | | H | F | CH₃ | CH₃ | O | MS: [M⁺] 336, 238 |
| 50 | H | —O—CF₂—O— | | H | F | | —(CH₂)₄— | O | mp. 125° C. |
| 51 | H | —N—CO—O—<br>   \|<br>   CH₂CN | | H | F | | —(CH₂)₄— | O | MS: [M⁺] 357,<br>233, 125 |
| 52 | H | —N—CO—O—<br>   \|<br>   CH₂CN | | H | F | | —(CH₂)₃— | O | ¹H-NMR (CDCl₃):<br>δ = 4.75(2);<br>7.10(1); 7.25(1) |
| 53 | H | OCH₂COOC₂H₅ | Cl | H | F | | —(CH₂)₄— | O | ¹H-NMR (CDCl₃):<br>δ = 1.25(3);<br>1.80(4); 2.45(4);<br>4.25(2) |
| 54 | H | OCH₂COOC₂H₅ | Cl | H | F | | —(CH₂)₃— | O | ¹H-NMR (CDCl₃):<br>δ = 1.25(3);<br>2.20(2); 2.80(4);<br>4.25(2) |
| 55 | H | OCH₂COOC₂H₅ | Cl | H | F | CH₃ | CH₃ | O | Oil |
| 56 | H | —N—CO—S—<br>   \|<br>   CH₂CN | | H | F | | —(CH₂)₄— | O | MS: [M⁺] 373 |
| 57 | H |      CH₃<br>     \|<br>—N—CO—CH—O—<br>   \|<br>   CH₂C≡CH | | H | H | | —(CH₂)₄— | O | mp. 217–227° C. |
| 58 | H | —N—CO—CH₂—O—<br>   \|<br>   CH₂CH=CH₂ | | H | F | | —(CH₂)₃— | O | mp. 208° C. |
| 59 | H | —N—CO—CH₂—O—<br>   \|<br>   CH₂CH=CH₂ | | H | F | CH₃ | H | O | mp. 196° C. |

TABLE 3-continued

Preparation examples of the compounds of the formula (I)

$$\text{(I)}$$

Structure: R⁷, R⁶, O, N, C=O, Q, attached to phenyl ring with R¹, R², R³, R⁴, R⁵

| Ex. No. | R¹ | R² | R³ | R⁴ | R⁵ | R⁶ | R⁷ | Q | Physical data |
|---|---|---|---|---|---|---|---|---|---|
| 60 | H | —N(CH₂CH=CH₂)—CO—CH₂—O— | | H | F | CH₃ | C₂H₅ | O | mp. 161° C. |
| 61 | H | —N(CH₂C≡CH)—CO—CH₂—O— | | H | H | CH₃ | C₂H₅ | O | mp. 278° C. |
| 62 | H | —N(CH₂C≡CH)—CO—CH₂—O— | | H | H | CH₃ | H | O | mp. 254° C. |
| 63 | H | —N(CH₂C≡CH)—CO—CH₂—O— | | H | F | CH₃ | C₂H₅ | O | mp. 195° C. |
| 64 | H | O(CH₂CH₂O)₂C₂H₅ | CN | H | F | | —(CH₂)₃— | O | |
| 65 | H | O(CH₂CH₂O)₂C₂H₅ | CN | H | F | CH₃ | C₂H₅ | O | mp. 77° C. |
| 66 | H | —N(CH₂C≡CH)—CO—S— | | H | F | | —(CH₂)₃— | O | mp. 218° C. |
| 67 | H | —N(CH₂C≡CH)—CO—S— | | H | F | CH₃ | C₂H₅ | O | mp. 227° C. |
| 68 | H | —N(CH₂C≡CH)—CO—S— | | H | F | | —(CH₂)₄— | O | mp. 139° C. |
| 69 | H | SCH₂COOC₂H₅ | Cl | H | F | | —(CH₂)₃— | O | |
| 70 | H | SCH₂COOC₂H₅ | Cl | H | F | CH₃ | C₂H₅ | O | |

(a) ¹H-NMR (80 Mhz, CDCl₃, δ): 8.10 (dd, 1H, J=8.0 Hz, J'=1.0 Hz); 7.83 (dt, 1H, J=8.0 Hz, J'=1.0 Hz); 7.46 (t, 1H, J=8.0 Hz); 7.41 (d, 1H, J=8.0 Hz); 7.33 (d, 1H, J=5.8 Hz); 6.98 (d, 1H, J=9.0 Hz); 4.73 (s, 2H); 4.6 (dd, 2H).
(b) ¹H-NMR (80 Mhz, CDCl₃, δ): 7.41 (d, 1H, J=9.5 Hz); 7.35 (d, 1H, J=5.8 Hz); 2.95–2.70 (m, 4H); 2.27–2.10 (m, 2H).
(c) ¹H-NMR (80 Mhz, CDCl₃, δ): 7.39 (d, 1H, J=9.5 Hz); 7.35 (d, 1H, J=6.25 Hz); 6.45 and 6.20 (dt, 1H, J=4.5 Hz, J'=4.5 Hz); 2.55–2.37 and 1.65–1.45 (m, 8H).

USE EXAMPLE

In the Use Example which follows, the compound listed below is used as comparison substance:

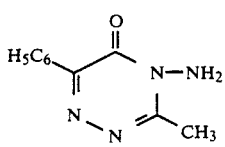
(A)

4-Amino-3-methyl-6-phenyl-4H-1,2,4-triazin-5-one (Metamitron, GOLTIX) —disclosed in DE-OS (German Published Specification) 2,364,474/Example 1.

EXAMPLE A

Post-emergence test

| | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, for example the compounds according to Preparation Examples (2) and (3) show a clearly superior activity compared with comparison substance (A).

It is understood that the specification and examples are illustrative but not limitative of the present invention and that other embodiments within the spirit and scope of the invention will suggest themselves to those skilled in the art.

We claim:

1. A method of combating unwanted vegetation which comprises applying to such vegetation or to a locus from which it is desired to exclude such vegetation a herbicidally effective amount of a compound of the formula

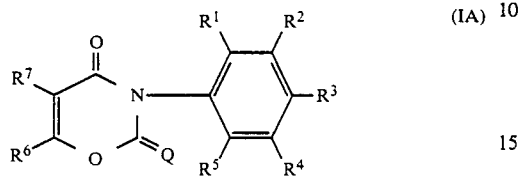

in which $R^1$ represents hydrogen or halogen, $R^2$ represents hydrogen, nitro, cyano, halogen, or represents a radical from the group consisting of $C_1$-$C_8$-alkyl, $C_1$-$C_6$-alkoxy, $C_1$-$C_6$-alkylthio and $C_1$-$C_6$-alkylamino, which radical is optionally substituted by fluorine, chlorine, bromine, cyano, $C_3$-$C_6$-cycloalkyl which is optionally substituted by fluorine, chlorine, bromine, methyl and/or ethyl, by $C_1$-$C_6$-alkoxy, $C_1$-$C_4$-alkoxy-$C_1$-$C_4$-alkoxy, $C_1$-$C_5$-alkylthio, $C_1$-$C_6$-alkylsulphinyl, $C_1$-$C_6$-alkylsulphonyl, $C_1$-$C_4$-alkylthio-$C_1$-$C_4$-alkoxy, $C_1$-$C_4$-alkylsulphonyl-$C_1$-$C_4$-alkoxy, $C_3$-$C_4$-alkenyloxy, $C_3$-$C_6$-alkinyloxy, $C_3$-$C_6$-alkenylthio, $C_3$-$C_6$-alkinylthio, carboxyl, $C_1$-$C_6$-alkoxy-carbonyl, $C_3$-$C_6$-alkenyloxy-carbonyl, $C_3$-$C_6$-alkinyloxy-carbonyl, $C_3$-$C_6$-cycloalkyloxy-carbonyl, $C_3$-$C_6$-cycloalkenyloxy-carbonyl, $C_3$-$C_6$-cycloalkyl-$C_1$-$C_4$-alkoxy-carbonyl, $C_3$-$C_6$-cycloalkenyl-$C_1$-$C_4$-alkoxycarbonyl, $C_1$-$C_4$-alkoxy-$C_1$-$C_4$-alkoxy-carbonyl, $C_1$-$C_4$-alkylthio-$C_1$-$C_4$-alkoxy-carbonyl, benzyloxy-$C_1$-$C_4$-alkoxy-carbonyl, $C_1$-$C_4$-alkoxy-carbonyl-$C_1$-$C_4$-alkoxycarbonyl, $C_1$-$C_4$-alkylamino-carbonyl-$C_1$-$C_4$-alkoxycarbonyl, di-($C_1$-$C_4$-alkyl)-amino-carbonyl-$C_1$-$C_4$-alkoxy-carbonyl, $C_1$-$C_4$-alkoxy-$C_1$-$C_4$-alkyl-aminocarbonyl, $C_1$-$C_4$-alkoxy-imino-$C_1$-$C_4$-alkyl, $C_3$-$C_4$-alkenyloxy-imino-$C_1$-$C_4$-alkyl, $C_1$-$C_4$-alkoxy-carbonyl-$C_1$-$C_4$-alkoxy-imino-$C_1$-$C_4$-alkyl, $C_1$-$C_6$-alkylthio-carbonyl, $C_3$-$C_6$-alkenylthio-carbonyl, $C_3$-$C_6$-alkinylthio-carbonyl, carbamoyl, $C_1$-$C_6$-alkylamino-carbonyl, $C_3$-$C_6$-alkenylamino-carbonyl, $C_3$-$C_4$-alkinylamino-carbonyl, di-($C_1$-$C_4$-alkyl)-amino-carbonyl, di-($C_3$-$C_4$-alkenyl)-amino-carbonyl and/or di-($C_3$-$C_4$-alkinyl)-aminocarbonyl, or represents a radical from the group consisting of $C_3$-$C_6$-alkenyl, $C_3$-$C_6$-alkinyl, $C_3$-$C_6$-alkenyloxy, $C_3$-$C_6$-alkinyloxy, $C_3$-$C_6$-alkenylthio, $C_3$-$C_6$-alkinylthio, $C_1$-$C_6$-alkylsulphinyl and $C_1$-$C_6$-alkylsulphonyl, which radical is optionally substituted by fluorine and/or chlorine, $R^3$ represents hydrogen, halogen, nitro, cyano, or represents a radical from the series comprising $C_1$-$C_4$-alkyl, $C_3$-$C_4$-alkenyl, $C_3$-$C_4$-alkinyl, $C_1$-$C_4$-alkoxy, $C_3$-$C_4$-alkenyloxy, $C_3$-$C_4$-alkinyloxy, $C_1$-$C_4$-alkylthio, $C_3$-$C_4$-alkenylthio, $C_3$-$C_4$-alkinylthio, $C_1$-$C_4$-alkylsulphinyl, $C_1$-$C_4$-alkylsulphenyl and $C_1$-$C_4$-alkylamino, which radical is optionally substituted by fluorine and/or chlorine, or the two radicals $R^2$ and $R^3$ together represent —O—$CH_2$—O—$CH_2$— or the group —X—(CO)$_n$—A—Y— where n represents the numbers 0 or 1, A represents a direct bond ore represents straight-chain or branched $C_1$-$C_4$-alkanediyl which is optionally substituted by fluorine and/or chlorine, X represents oxygen, sulphur or the group N—$R^2$ where $R^3$ represents hydrogen or radicals from the group consisting of $C_1$-$C_4$-alkyl, $C_3$-$C_4$-alkenyl and $C_3$-$C_4$-alkinyl, which radicals are optionally substituted by fluorine and/or chlorine, cyano, $C_1$-$C_4$-alkoxy, $C_1$-$C_4$-alkoxy-carbonyl or pyridiyl, and Y represents oxygen or sulphur, in which furthermore $R^4$ represents hydrogen or halogen, $R^5$ represents hydrogen or halogen, $R^6$ represents hydrogen, halogen or $C_1$-$C_4$-alkyl which is optionally substituted by fluorine and/or chlorine, $R^7$ represents hydrogen, halogen or $C_1$-$C_4$-alkyl which is optionally substituted by fluorine and/or chlorine, or the two radicals $R^6$ and $R^7$ together represent straight-chain or branched $C_3$-$C_5$-alkanediyl or together with the carbon atoms to which they are bonded form a benzo group, and Q represents oxygen or sulphur, with the proviso that at least three of the radicals $R^1$ to $R^5$ are other than hydrogen.

2. The method according to claim 1, in which $R^1$ represents hydrogen, $R^2$ represents hydrogen, nitro, cyano, fluorine, chlorine or bromine, or represents a radical from the group consisting of $C_1$-$C_4$-alkyl, $C_1$-$C_4$-alkoxy, $C_1$-$C_4$-alkylthio and $C_1$-$C_4$-alkylamino, which radical is optionally substituted by fluorine, chlorine, cyclopropyl which can be substituted by chlorine and/or methyl; by $C_1$-$C_4$-alkoxy, $C_1$-$C_4$-alkylthio, $C_1$-$C_4$-alkylsulphinyl, $C_1$-$C_4$-alkylsulphonyl, $C_3$-$C_4$-alkenyloxy, $C_3$-$C_4$-alkinyloxy, $C_3$-$C_4$-alkenylthio, $C_3$-$C_4$-alkinylthio, carboxyl, $C_1$-$C_4$-alkoxy-carbonyl, $C_3$-$C_4$-alkenyloxy-carbonyl, $C_3$-$C_4$-alkinyloxy-carbonyl, $C_3$-$C_6$-cycloalkyloxy-carbonyl, $C_3$-$C_6$-cycloalkyl-$C_1$-$C_2$-alkoxycarbonyl, $C_1$-$C_4$-alkoxy-$C_1$-$C_2$-alkoxy-carbonyl, $C_1$-$C_4$-alkylthio-$C_1$-$C_2$-alkoxy-carbonyl, $C_1$-$C_4$-alkoxy-carbonyl or $C_1$-$C_4$-alkylaminocarbonyl, di-($C_1$-$C_2$-alkyl)-aminocarbonyl, $C_1$-$C_2$-alkoxy-$C_1$-$C_2$-alkyl-amino-carbonyl, $C_3$-$C_4$-alkenyloxy-imino-$C_1$-$C_2$-alkyl, $C_1$-$C_2$-alkoxy-imino-$C_1$-$C_2$-alkyl, $C_1$-$C_2$-alkoxy-carbonyl-$C_1$-$C_2$-alkoxy-imino-$C_1$-$C_2$-alkyl, or represents a radical from the group consisting of $C_3$-$C_4$-alkenyloxy, $C_3$-$C_4$-alkinyloxy, $C_3$-$C_4$-alkenylthio and $C_3$-$C_4$-alkinylthio, which radical is optionally substituted by fluorine and/or chlorine, $R^3$ represents hydrogen, fluorine, chlorine, bromine, cyano, methyl or trifluoromethyl, or the two radicals $R^2$ and $R^3$ together represent —O—$CH_2$—O—$CH_2$— or the group —X—(CO)$_n$—A—Y—where n represents the numbers 0 or 1, A represents a direct bond or represents methylene, ethylene, propylene or butylene, X represents oxygen or the group N—$R^8$ where $R^8$ represents hydrogen, $C_1$–$C_4$-alkyl, $C_3$–$C_4$-alkenyl or $C_3$–$C_4$-alkinyl, and Y represents oxygen, in which furthermore $R^4$ represents hydrogen, $R^5$ represents hydrogen, fluorine or chlorine $R^6$ represents hydrogen, chlorine, bromine, methyl, ethyl, propyl, isopropyl or trifluoromethyl, $R^7$ represents hydrogen, chlorine, bromine, methyl, ethyl, propyl, isopropyl or trifluoromethyl, or the two radicals $R^6$ and $R^7$ together represent straight-chain or branched $C_3$–$C_5$-alkanediyl or together with the carbon atoms to which they are bonded form a benzo group, and Q represents oxygen or sulphur.

3. The method according to claim 1, wherein such compound is 3-(2-fluoro-4-methyl-5-isopropoxy-phenyl)-2,3,4,5,6,7-hexahydrocyclopenta[e]-1,3-oxazine-2,4-dione of the formula

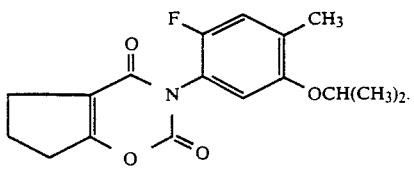

4. The method according to claim 1, wherein such compound is 2,3,4,5,6,7,8-heptahydro-3-(2,4-dichloro-5-isopropoxy-phenyl)cyclohexa-1,3-oxazin-2,4-dione of the formula

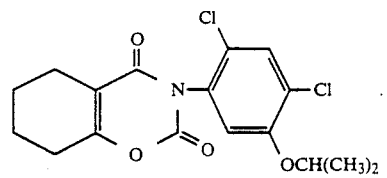

5. The method according to claim 1, in which $R^6$ represents hydrogen, halogen or $C_1$–$C_4$-alkyl which is optionally substituted by fluorine and/or chlorine, and $R^7$ represents hydrogen, halogen or $C_1$–$C_4$-alkyl which is optionally substituted by fluorine and/or chlorine.

* * * * *

UNITED STATES PATENT AND TRADEMARK OFFICE
CERTIFICATE OF CORRECTION

PATENT NO. : 5,061,310
DATED : October 29, 1991
INVENTOR(S) : Ooms et al

It is certified that error appears in the above-indentified patent and that said Letters Patent is hereby corrected as shown below:

Col. 47, line 66  Delete " alkylsulphenyl " and substitute -- alkylsulphonyl --

Col. 48, line 4   Delete " ore " and substitute -- or --

Col. 48, line 8   Delete " N-$R^2$ " and substitute -- N-$R^8$ --

Col. 48, line 10  Delete " $R^3$ " and substitute -- $R^8$ --

Col. 50, line 12  After " -phenyl) " delete " cyclohexa " and substitute -- -cyclohexa[e] --

Signed and Sealed this

Eighth Day of February, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,061,310

DATED : October 29, 1991

INVENTOR(S) : Ooms, et al.

It is certified that error appears in the above-identified patent and that said Letters Patent is hereby corrected as shown below:

Col. 47, line 28  Delete " $C_1$-$C_5$-alkylthio " and substitute -- $C_1$-$C_6$-alkylthio --

Col. 47, line 31  Delete " $C_3$-$C_4$-alkenyloxy " and substitute -- $C_3$-$C_6$-alkenyloxy --

Col. 47, line 50  Delete " $C_3$-$C_4$-alkinylamino " and substitute -- $C_3$-$C_6$-alkinylamino --

Signed and Sealed this

Thirty-first Day of January, 1995

Attest:

BRUCE LEHMAN

*Attesting Officer*  *Commissioner of Patents and Trademarks*